(12) United States Patent
Derdzinski et al.

(10) Patent No.: US 12,390,131 B2
(45) Date of Patent: Aug. 19, 2025

(54) GLUCOSE MEASUREMENT PREDICTIONS USING STACKED MACHINE LEARNING MODELS

(71) Applicant: DexCom, Inc., San Diego, CA (US)

(72) Inventors: Mark Derdzinski, La Jolla, CA (US); Joost van der Linden, San Diego, CA (US); Robert Dowd, San Diego, CA (US); Lauren Hruby Jepson, San Diego, CA (US); Giada Acciaroli, Edinburgh (GB)

(73) Assignee: Dexcom, Inc., San Diego, CA (US)

( * ) Notice: Subject to any disclaimer, the term of this patent is extended or adjusted under 35 U.S.C. 154(b) by 148 days.

(21) Appl. No.: 17/334,448

(22) Filed: May 28, 2021

(65) Prior Publication Data

US 2021/0378563 A1 Dec. 9, 2021

Related U.S. Application Data

(60) Provisional application No. 63/034,257, filed on Jun. 3, 2020.

(51) Int. Cl.
*A61B 5/145* (2006.01)
*A61B 5/00* (2006.01)

(52) U.S. Cl.
CPC ........ *A61B 5/14532* (2013.01); *A61B 5/0004* (2013.01); *A61B 5/0022* (2013.01);
(Continued)

(58) Field of Classification Search
CPC . A61B 5/14532; A61B 5/0004; A61B 5/0022; A61B 5/6801; A61B 5/7225;
(Continued)

(56) References Cited

U.S. PATENT DOCUMENTS

2007/0168136 A1* 7/2007 Booth ................. A61M 5/1723
600/300
2012/0123234 A1 5/2012 Atlas et al.
(Continued)

FOREIGN PATENT DOCUMENTS

CA 3142003 A1 12/2020
EP 4162507 A1 4/2023
(Continued)

OTHER PUBLICATIONS

International Search Report and Written Opinion for Application No. PCT/US2021/035233, mailed Oct. 14, 2021, 12 pages.
(Continued)

*Primary Examiner* — Aurelie H Tu
(74) *Attorney, Agent, or Firm* — PATTERSON + SHERIDAN, LLP

(57) ABSTRACT

Glucose measurement and glucose-impacting event prediction using a stack of machine learning models is described. A CGM platform includes stacked machine learning models, such that an output generated by one of the machine learning models can be provided as input to another one of the machine learning models. The multiple machine learning models include at least one model trained to generate a glucose measurement prediction and another model trained to generate an event prediction, for an upcoming time interval. Each of the stacked machine learning models is configured to generate its respective output when provided as input at least one of glucose measurements provided by a CGM system worn by the user or additional data describing user behavior or other aspects that impact a person's
(Continued)

glucose in the future. Predictions may then be output, such as via communication and/or display of a notification about the corresponding prediction.

20 Claims, 16 Drawing Sheets

(52) U.S. Cl.
CPC .......... *A61B 5/6801* (2013.01); *A61B 5/7225* (2013.01); *A61B 5/7267* (2013.01); *A61B 5/7275* (2013.01); *A61B 5/74* (2013.01)

(58) Field of Classification Search
CPC ....... A61B 5/7267; A61B 5/7275; A61B 5/74; A61B 5/6833; G06N 3/044; G06N 3/08; G06N 20/20; G16H 50/20; G16H 50/70
See application file for complete search history.

(56) References Cited

U.S. PATENT DOCUMENTS

| | | |
|---|---|---|
| 2018/0169333 A1 | 6/2018 | Grosman et al. |
| 2018/0174675 A1 | 6/2018 | Roy et al. |
| 2018/0272063 A1 | 9/2018 | Neemuchwala et al. |
| 2018/0272066 A1 | 9/2018 | McMahon et al. |
| 2019/0246914 A1 | 8/2019 | Constantin et al. |
| 2020/0093988 A1 | 3/2020 | Zhong et al. |
| 2020/0375549 A1 | 12/2020 | Wexler et al. |
| 2021/0038163 A1 | 2/2021 | Agrawal et al. |
| 2021/0315525 A1* | 10/2021 | Mairs .................... G16H 10/60 |

FOREIGN PATENT DOCUMENTS

| | | |
|---|---|---|
| JP | 2012058939 A | 3/2012 |
| JP | 2020031701 A | 3/2020 |

OTHER PUBLICATIONS

Khadem H. et al., "Multi-lag Stacking for Blood Glucose Level Prediction,". In Knowledge Discovery in Healthcare Data 2020; CEUR—Workshop Proceedings 17. Sep. 2020; vol. 2675, pp. 146-150.

Patil K. et al., "Designing a Model to Detect Diabetes using Machine Learning," Int J Engin Res Tech., Nov. 2019, vol. 8, No. 11, pp. 333-340.

Wang Y. et al., "A Novel Adaptive-Weighted-Average Framework for Blood Glucose Prediction." Diabetes Tech Therapeutics, Oct. 2013, vol. 15, No. 10, pp. 792-801.

* cited by examiner

GLUCOSE MEASUREMENT PREDICTIONS USING STACKED MACHINE LEARNING MODELS

INCORPORATION BY REFERENCE TO RELATED APPLICATIONS

Any and all priority claims identified in the Application Data Sheet, or any correction thereto, are hereby incorporated by reference under 37 CFR 1.57. This application claims the benefit of U.S. Provisional Application No. 63/034,257, filed Jun. 3, 2020. Each of the aforementioned application(s) is incorporated by reference herein in its entirety, and each is hereby expressly made a part of this specification.

BACKGROUND

Diabetes is a metabolic condition affecting hundreds of millions of people, and is one of the leading causes of death worldwide. For people living with diabetes, access to treatment is critical to their survival. With proper treatment, serious damage to the heart, blood vessels, eyes, kidneys, and nerves, due to diabetes can be largely avoided. Proper treatment for a person with Type I diabetes generally involves monitoring glucose levels throughout the day and regulating those levels—with some combination of insulin, eating, and exercise—so that the levels stay within a desired range. With advances in medical technologies a variety of systems for monitoring glucose levels have been developed. While monitoring a person's current glucose level is useful for deciding how to treat diabetes, knowing what the person's glucose levels will be in the future is more useful. This is because it allows the person or a caregiver to take actions to mitigate potentially adverse health conditions, tied to changing glucose levels, before such health conditions occur. However, conventional techniques and systems for generating glucose level predictions suffer from inaccuracies due to the limited information considered in generating such glucose level predictions.

For instance, a system employing conventional glucose prediction techniques may generate a glucose level prediction that accounts only for historical glucose measurements as input. However, a user's historical glucose levels (e.g., a glucose trace spanning the past 12 hours) alone may not accurately represent different factors that will affect the user's glucose levels over an upcoming time interval, particularly when the user will participate in, or otherwise be subject to, an event that impacts their glucose levels (e.g., a meal, exercise, insulin administration, etc.) in the upcoming interval. Failure of conventional systems to account for these events and additional information beyond historical glucose levels alone thus result in generating inaccurate glucose level predictions, which can misinform a user as to their glucose response and result in dangerous health conditions.

SUMMARY

To overcome these problems, glucose measurement prediction and glucose-impacting event prediction using a stack of multiple machine learning models is leveraged. Given the number of people that wear continuous glucose monitoring (CGM) systems and because CGM systems produce measurements continuously, a CGM platform that provides a CGM system with a sensor for detecting glucose levels, and maintains measurements produced by such a system may have an enormous amount of data, e.g., hundreds of millions of patient days' worth of measurements. However, this amount of data is practically, if not actually, impossible for a human to process to reliably identify patterns of a robust number of state spaces.

In one or more implementations, a CGM platform includes multiple machine learning models arranged in a stacked configuration, such that an output generated by one of the machine learning models can be provided as input to another one of the machine learning models for use in generating its output. In some implementations, the multiple machine learning models include at least one model trained to generate a glucose measurement prediction and another model trained to generate an event prediction for an upcoming time interval. One or more of the stacked machine learning models may be configured to generate its respective output when provided as input glucose measurements obtained from a CGM system worn by the user. Alternatively or additionally, the stacked machine learning models may be configured to generate their respective outputs when provided as input additional data describing one or more other aspects that impact a person's glucose in the future, such as application usage activity, insulin administered, exercise, and so forth.

By leveraging the multiple machine learning models in the stacked configuration, this additional data may in some implementations be obtained from an output of one of those multiple machine learning models. Outputs of various ones of the multiple machine learning models may be selectively provided as input to other ones of the models based on a confidence value associated with the output to ensure that only reliable predictions are used to influence other predictions generated by the stacked model configuration. Glucose measurement predictions and event predictions may then be output, such as via communication and/or display of a notification about the corresponding prediction.

This Summary introduces a selection of concepts in a simplified form that are further described below in the Detailed Description. As such, this Summary is not intended to identify essential features of the claimed subject matter, nor is it intended to be used as an aid in determining the scope of the claimed subject matter.

BRIEF DESCRIPTION OF THE DRAWINGS

The detailed description is described with reference to the accompanying figures.

DETAILED DESCRIPTION

Overview

Figure 1:
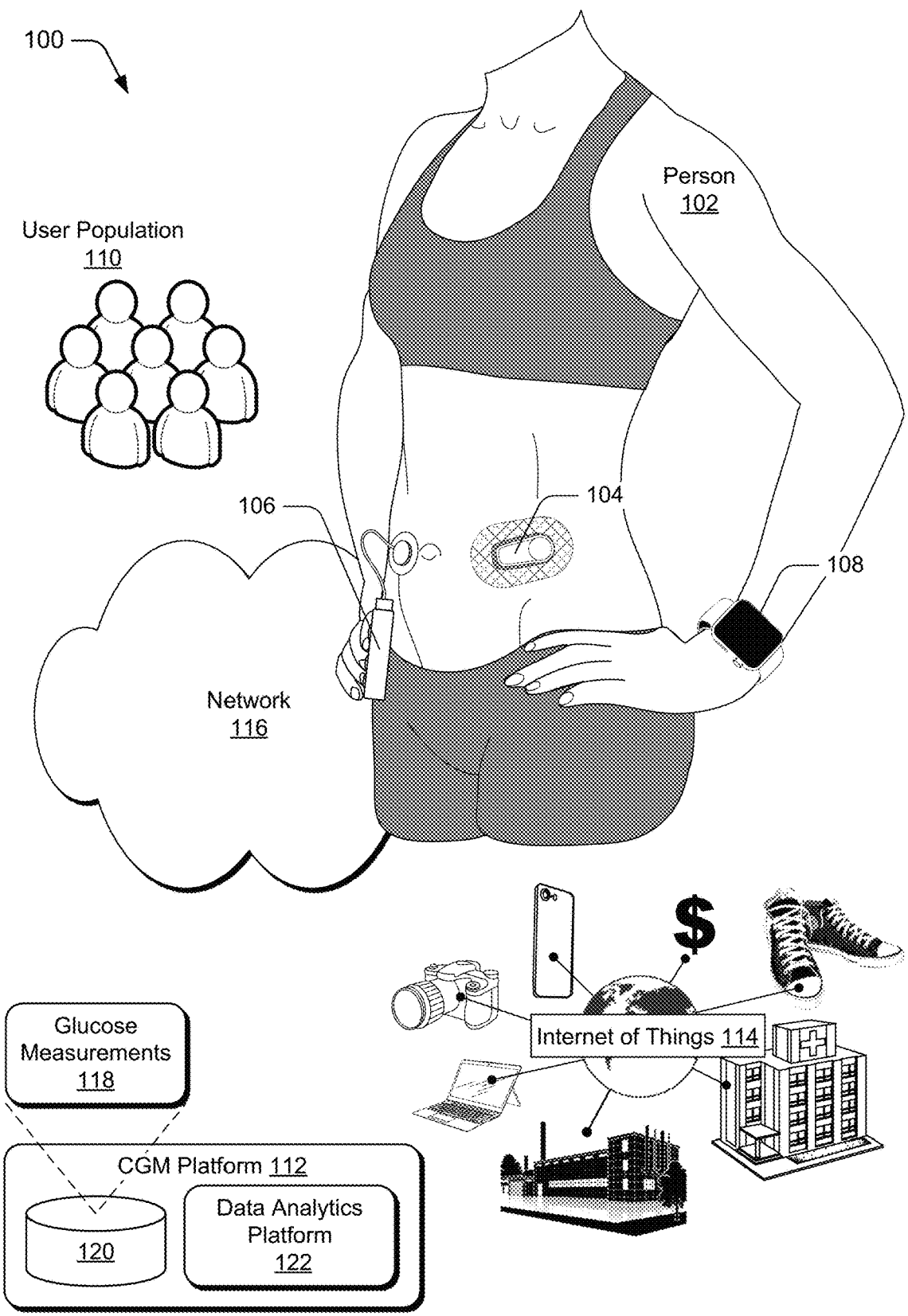
FIG. 1 is an illustration of an environment in an example implementation that is operable to employ techniques described herein.

Monitoring glucose levels is useful in the treatment of diabetes, such as to identify when an individual is subject to potentially adverse health conditions associated with problematic glucose levels (e.g., hyper- or hypo-glycemia). In this manner, the ability to predict the individual's future glucose levels is particularly advantageous, because it allows the individual or a caregiver to take corrective action to mitigate such adverse health conditions before they occur.

Conventional approaches to predicting future glucose levels are limited in that they consider only historical glucose information (e.g., applying regression models to historical glucose information in order to extrapolate future glucose level predictions). Such conventional approaches consequently fail to account for the occurrence of events and other factors that affect an individual's glucose level, such as occurrence of an event that is not labeled in the historical glucose information, and thus unaccounted for in predicting future glucose levels.

For instance, a drop in glucose levels, as indicated in historical glucose information, may correspond to a variety of different events (e.g., exercise, insulin administration, etc.). While each event may be generally characterized by a drop in glucose levels, a person's response to different ones of these events can vary drastically. For example, the person's glucose levels may exhibit one response following insulin administration and a significantly different response following a workout. Predicting future glucose levels without differentiating between the different responses (e.g., considering a drop in glucose measurements alone, without respect to the person's different responses to insulin administration and exercise) may result in significant miscalculations, which in turn can have drastic consequences.

Continuing this example, the person's glucose levels may historically drop for longer periods of time following a standard dose of insulin in contrast to historical drops in glucose levels following exercise. Conventional approaches that fail to account for different event responses, or incorrectly associate a glucose level drop with a certain event, thus generate inaccurate glucose level predictions. Consequently, inaccurate glucose level predictions may result in recommending incorrect insulin doses (e.g., a lower dose of insulin that is insufficient to cover a future glucose spike not represented by the glucose level predictions). Similarly, the accuracy associated with these conventional approaches degrades as a time associated with the predicted glucose levels moves further and further into the future, relative to a current time.

To overcome these problems, glucose prediction using multiple machine learning models arranged in a stacked configuration is leveraged. Each of the stacked machine learning models may be configured according to a variety of machine learning models, such as neural networks (e.g., recurrent neural networks such as long-short term memory (LSTM) networks), state machines, Monte Carlo methods, particle filters, reinforcement learning algorithms (e.g., Markov decision process), and regression models, to name just a few.

In one or more implementations, a continuous glucose monitoring (CGM) platform includes this stack of machine learning models, where at least one model of the stack is configured to generate glucose measurement predictions for an individual user based on training involving historical glucose measurements of a user population. In some implementations, this model may further be configured to receive as input additional data describing one or more factors that can affect the individual user's glucose levels, which may be received from storage or from one or more other machine learning models in the stack, as described in more detail below. The glucose measurements of the user population and the individual user may be provided by CGM systems worn by users of the user population and the individual user. By obtaining measurements produced by these CGM systems and maintaining the measurements, the CGM platform may have an enormous amount of data (e.g., hundreds of millions of patient days' worth of measurements) that conventional systems are unable to process.

In accordance with these implementations, the stack further includes at least one machine learning model configured to generate an event prediction describing whether a certain event is likely to occur in the future, given one or more of the historical glucose measurements, the glucose measurement prediction(s), or the additional data as input. For instance, the stack may include one machine learning model configured to predict whether an individual will eat a meal during a designated time period, another model configured to predict whether the individual will exercise during the designated time period, another model configured to predict whether the individual will administer insulin during the designated time period, another model to predict whether the individual will sleep or rest during the designated time period, another model to predict whether the individual will be subject to stress during the future time period, another model to predict the individual's glucose during the designated time period, and so forth. In some implementations, the designated time period may correspond to a current time, such that the event prediction corresponds to a prediction of whether a whether a certain event is currently occurring.

In addition to predicting whether a certain event is currently occurring and/or likely to occur in the future, each of the stacked machine learning models may further be configured to predict one or more values that describe particular characteristics and/or attributes of a respective event, which in turn are useable to predict how a particular individual will respond to the event (e.g., predict how the individual's glucose levels will change as a result of the event). For instance, in addition to or alternatively from predicting whether an individual will eat a meal, a machine learning model may be configured to predict a caloric intake associated with the meal and/or the individual's anticipated glucose response to the caloric intake. As another example, in addition to or alternatively from predicting whether the individual will sleep, a machine learning model may be configured to predict a sleep score indicating a quality of the sleep (e.g., duration, ratio of rapid eye movement (REM) sleep to non-REM sleep, etc.) and/or the individual's anticipated glucose response to such sleep that corresponds to the score. In a further example, in addition to or alternatively from predicting whether an exercise event will occur, a machine learning model may be configured to predict information describing an individual's vital characteristics during and after the event (e.g., heart rate, body temperature, etc.) and/or corresponding glucose level changes based on these vital characteristics. In this manner, machine learning models described herein may be configured to predict whether an event will occur during a future time interval as well as or alternatively characteristics and/or attributes of the event that may influence an individual's glucose levels.

By virtue of their arrangement in the stacked configuration, a prediction output by one machine learning model of the stack may be provided as input to one or more other machine learning models of the stack (e.g., a machine learning model configured to generate the glucose measurement predictions), thereby enabling consideration of various factors that affect glucose levels beyond historical glucose measurements.

One or more of the machine learning models of the stack thus may be configured to generate its respective prediction after being trained with one or more of historical glucose measurements of the user population or additional data describing user behavior relative to various events. In one or more implementations, those models or different models of the stacked machine learning models may be configured to generate a respective prediction with information indicative of a confidence value associated with the prediction. Predictions can then be selectively provided as input to machine learning models of the stack based on their associated confidence values, such that downstream models in the stack are only provided with predictions as input when the predictions have associated confidence values that satisfy a confidence threshold. In this manner, the stacked configuration improves accuracies associated with generated predictions by precluding the machine learning models from considering input information that does not accurately reflect actual, observed events.

Glucose measurement predictions and event predictions generated by the stacked machine learning models can then be output, such as for generating a notification about the upcoming glucose measurements or events. This notification may be communicated over a network to one or more computing devices, including a computing device associated with the user (e.g., for output via an application of the CGM platform), a computing device associated with a health care provider, or a computing device associated with a telemedicine service, to name just a few. In some implementations, the notification is accompanied with a prompt for feedback regarding the associated prediction, which is useable by the CGM system to refine model parameters, refine event profiles, and improve accuracies associated with individual model outputs.

By predicting upcoming events that affect glucose and upcoming glucose measurements, and notifying users, health care providers, and/or telemedicine services about the upcoming glucose measurements, the described stacked machine learning models enable actions to be taken to mitigate potentially adverse health conditions before those health conditions occur. Advantageously, the more accurate and timely predictions of upcoming glucose provided by the stacked machine learning models allow users and various other parties to make better informed decisions regarding how to treat diabetes and achieve better outcomes through the treatment. In so doing, serious damage to the heart, blood vessels, eyes, kidneys, and nerves, and death due to diabetes can be largely avoided.

In the following description, an example environment is first described that may employ the techniques described herein. Example implementation details and procedures are then described which may be performed in the example environment as well as other environments. Performance of the example procedures is not limited to the example environment and the example environment is not limited to performance of the example procedures.

Example Environment

FIG. 1 illustrates an environment 100 in an example implementation that is operable to employ glucose measurement prediction and event prediction using stacked machine learning models described herein. The illustrated environment 100 includes person 102, who is depicted wearing a continuous glucose monitoring (CGM) system 104, insulin delivery system 106, and computing device 108. The illustrated environment 100 also includes other users in a user population 110 of the CGM system, CGM platform 112, and Internet of Things 114 (IoT 114). The CGM system 104, insulin delivery system 106, computing device 108, user population 110, CGM platform 112, and IoT 114 are communicatively coupled, including via a network 116.

Alternatively or additionally, one or more of the CGM system 104, the insulin delivery system 106, or the computing device 108 may be communicatively coupled in other ways, such as using one or more wireless communication protocols and/or techniques. By way of example, the CGM system 104, the insulin delivery system 106, and the computing device 108 may communicate with one another using one or more of Bluetooth (e.g., Bluetooth Low Energy links), near-field communication (NFC), 5G, and so forth. The CGM system 104, the insulin delivery system 106, and the computing device 108 may leverage various types of communication to form a closed-loop system between one another. In this way, the insulin delivery system 106 may deliver insulin based on sequences of glucose measurements in real-time as glucose measurements are obtained by the CGM system 104 and as glucose measurement predictions are generated.

In accordance with the described techniques, the CGM system 104 is configured to continuously monitor glucose of the person 102. The CGM system 104 may be configured with a CGM sensor, for instance, that continuously detects analytes indicative of the person 102's glucose and enables generation of glucose measurements. In the illustrated environment 100, these measurements are represented as glucose measurements 118. This functionality and further aspects of the CGM system 104's configuration are described in further detail below with respect to FIG. 2.

In one or more implementations, the CGM system 104 transmits the glucose measurements 118 to the computing device 108, via one or more of the communication protocols described herein, such as via wireless communication. The CGM system 104 may communicate these measurements in real-time (e.g., as the glucose measurements 118 are produced) using a CGM sensor. Alternatively or additionally, the CGM system 104 may communicate the glucose measurements 118 to the computing device 108 at designated intervals (e.g., every 30 seconds, every minute, every 5 minutes, every hour, every 6 hours, every day, and so forth). In some implementations, the CGM system 104 may communicate glucose measurements responsive to a request from the computing device 108 (e.g., a request initiated when the computing device 108 generates glucose measurement predictions for the person 102, a request initiated when displaying a user interface conveying information about the person 102's glucose measurements, and so forth). Accordingly, the computing device 108 may maintain the glucose measurements 118 of the person 102 at least temporarily (e.g., by storing glucose measurements 118 in computer-readable storage media, as described in further detail below with respect to FIG. 12).

Although illustrated as a wearable device (e.g., a smart watch), the computing device 108 may be configured in a variety of ways without departing from the spirit or scope of the described techniques. By way of example and not limitation, the computing device 108 may be configured as a different type of mobile device (e.g., a mobile phone or tablet device). In one or more implementations, the computing device 108 may be configured as a dedicated device associated with the CGM platform 112 (e.g., a device supporting functionality to obtain the glucose measurements 118 from the CGM system 104, perform various computations in relation to the glucose measurements 118, display information related to the glucose measurements 118 and the CGM platform 112, communicate the glucose measurements 118 to the CGM platform 112, combinations thereof, and so forth). In contrast to implementations where the computing device 108 is configured as a mobile phone, however, the computing device 108 may exclude functionality otherwise available with mobile phone or wearable configurations when configured as a dedicated CGM device, such as functionality to make phone calls, capture images, utilize social networking applications, and the like.

In some implementations, the computing device 108 is representative of more than one device. For instance, the computing device 108 may be representative of both a wearable device (e.g., a smart watch) and a mobile phone. In such multiple device implementations, different ones of the multiple devices may be capable of performing at least some of the same operations, such as receiving the glucose measurements 118 from the CGM system 104, communicating the glucose measurements 118 to the CGM platform 112 via the network 116, displaying information related to the glucose measurements 118, and so forth. Alternatively or additionally, different devices in the multiple device implementations may support different capabilities relative to one another, such as capabilities that are limited by computing instructions to specific devices.

In the example implementation where the computing device 108 represents separate devices, (e.g., a smart watch and a mobile phone) one device may be configured with various sensors and functionality to measure a variety of physiological markers (e.g., heartrate, breathing, rate of blood flow, and so on) and activities (e.g., steps, elevation changes, and the like) of the person 102. In this example multiple device implementation, another device may not be configured with such sensors or functionality, or may include a limited amount of such sensors or functionality. For instance, one of the multiple devices may have capabilities not supported by another one of the multiple devices, such as a camera to capture images of meals useable to predict future glucose levels, an amount of computing resources (e.g., battery life, processing speed, etc.) that enables a device to efficiently perform computations in relation to the glucose measurements 118. Even in scenarios where one of the multiple devices (e.g., a smart phone) is capable of carrying out such computations, computing instructions may limit performance of those computations to one of the multiple devices, so as not to burden multiple devices with redundant computations, and to more efficiently utilize available resources. To this extent, the computing device 108 may be configured in different ways and represent different numbers of devices beyond the specific example implementations described herein.

As mentioned above, the computing device 108 communicates the glucose measurements 118 to the CGM platform 112. In the illustrated environment 100, the glucose measurements 118 are depicted as being stored in storage device 120 of the CGM platform 112. The storage device 120 is representative of one or more types of storage (e.g., databases) capable of storing the glucose measurements 118. In this manner, the storage device 120 may be configured to store a variety of other data in addition to the glucose measurements 118. For instance, in accordance with one or more implementations, the person 102 represents a user of at least the CGM platform 112 and one or more other services (e.g., services offered by one or more third party service providers). In this manner, the person 102 may be associated with personally attributable information (e.g., a username) and may be required, at some time, to provide authentication information (e.g., password, biometric data, telemedicine service information, and so forth) to access the CGM platform 112 using the personally attributable information. This personally attributable information, authentication information, and other information pertaining to the person 102 (e.g., demographic information, health care provider information, payment information, prescription information, health indicators, user preferences, account information associated with a wearable device, social network account information, other service provider information, and the like) may be maintained in the storage device 120.

The storage device 120 is further configured to maintain data pertaining to other users in the user population 110. Given this, the glucose measurements 118 in the storage device 120 may include the glucose measurements from a CGM sensor of the CGM system 104 worn by the person 102 and also include glucose measurements from CGM sensors of CGM systems worn by other persons represented in the user population 110. In a similar manner, the glucose measurements 118 of these other persons of the user population 110 may be communicated by respective devices via the network 116 to the CGM platform 112, such that other persons are associated with respective user profiles in the CGM platform 112.

The data analytics platform 122 represents functionality to process the glucose measurements 118—alone and/or along with other data maintained in the storage device 120—to generate a variety of predictions, such as by using a stacked configuration of various machine learning models. Based on these predictions, the CGM platform 112 may provide notifications in relation to the predictions (e.g., alerts, recommendations, or other information generated based on the predictions). For instance, the CGM platform 112 may provide notifications to the person 102, to a medical professional associated with the person 102, combinations thereof, and so forth. Although depicted as separate from the computing device 108, portions or an entirety of the data analytics platform 122 may alternatively or additionally be implemented at the computing device 108. The data analytics platform 122 may also generate predictions using additional data obtained via the IoT 114.

For instance, in accordance with one or more implementations, the data analytics platform 122 is configured to generate glucose measurement predictions for the person 102, along with event predictions for events pertaining to the person 102, based on the glucose measurements 118 and additional information, such as information received from the IoT 114. For example, the data analytics platform 122 may implement a plurality of machine learning models in a stacked configuration, where each machine learning model is configured to output a different prediction (e.g., glucose measurement predictions, insulin administration event predictions, exercise predictions, meal predictions, and so forth). By leveraging such a stacked configuration of machine learning models, the data analytics platform 122 is configured to consider various factors that impact glucose levels of the person 102, thereby providing more accurate glucose measurement predictions relative to conventional approaches that consider only glucose measurements as input. Predictions generated by individual ones of the stacked machine learning models can be selectively provided as input to at least one of the other models (e.g., as input to a machine learning model that is downstream in the stacked configuration) to improve an accuracy of glucose measurement predictions.

For instance, in an example scenario where the stacked configuration includes multiple machine learning model that are individually configured to generate a different prediction (e.g., a person's glucose response to an upcoming insulin administration, the person's glucose response to upcoming exercise, the person's glucose response to an upcoming meal, and the person's upcoming glucose measurements), prediction information can be selectively provided as input to the stack of machine learning models based on various criteria, such as a confidence level associated with a respective prediction. By providing this prediction information as input along with glucose measurements 118 and additional data describing a person's behavior, the stacked configuration of machine learning models can reliably output glucose measurement predictions as well as predictions of upcoming events that may affect glucose levels.

For instance, one such model of the stacked configuration may process glucose measurements 118 and additional data pertaining to a person 102 to predict whether the person 102 will have an upcoming insulin administration event that may affect values of a glucose measurement prediction for a given time step and in a particular manner Another such model may predict whether the person 102 will have an upcoming exercise event and another such model may predict whether the person 102 will have an upcoming meal event that affect values of the glucose measurement prediction for the time step as well as how each particular event affects the values. Via arrangement in the stacked configuration, output predictions of one model may be used to influence predictions of other models.

For instance, if one model predicts with high confidence that the person 102 will exercise over an upcoming time period, that prediction may be provided as input to a second model configured to predict whether the person 102 will administer insulin over the upcoming time period and a third model configured to predict whether the person 102 will consume a meal over the upcoming time period. In this example scenario, output predictions of the second and third models may be influenced by the exercise event prediction of the first model and additional data describing historical behavior for the person 102, indicating that the person 102 is unlikely to be eating or administering insulin while exercising.

Predictions output by one stacked machine learning model may be selectively provided as input to other ones of the stacked machine learning models based on a confidence value associated with the prediction, such that low-confidence (e.g., less than 90% confidence) output predictions do not negatively impact predictions generated by other machine learning models in the stacked configuration. In some implementations, a confidence level or value associated with a prediction can be influenced by explicit user feedback from the person 102 to which the prediction pertains. For instance, if the data analytics platform 122 predicts that the person 102 may have an upcoming insulin administration event, the prediction can be output to the person 102 (e.g., via computing device 108) with a prompt for confirmation that the insulin administration event is going to occur.

If the person 102's response confirms that the insulin administration event is forthcoming, the confidence level associated with the predicted insulin administration event can be set to 100% and a predicted glucose level response associated with the predicted insulin administration event can be provided as input to different machine learning models in the stacked configuration. In contrast, if the person 102's response indicates that no insulin administration event is forthcoming, the prediction of the upcoming insulin administration event can be discarded to avoid improperly influencing the output predictions generated by different machine learning models. In this manner, the data analytics platform 122 is configured to leverage various factors in addition to the person 102's previous glucose levels to more accurately generate glucose measurement predictions.

To supply some of this additional information beyond previous glucose measurements, the IoT 114 is representative of various sources capable of providing data that describes the person 102 and the person 102's activity as a user of one or more service providers and activity with the real world. By way of example, the IoT 114 may include various devices of the user (e.g., cameras, mobile phones, laptops, exercise equipment, and so forth). To this end, the IoT 114 may provide information about interaction of the user with various devices (e.g., interaction with web-based applications, photos taken, communications with other users, and so forth). The IoT 114 may also include various real-world articles (e.g., shoes, clothing, sporting equipment, appliances, automobiles, etc.) configured with sensors to provide information describing behavior, such as steps taken, force of a foot striking the ground, length of stride, temperature of a user (and other physiological measurements), temperature of a user's surroundings, types of food stored in a refrigerator, types of food removed from a refrigerator, driving habits, and so forth. The IoT 114 may also include third parties to the CGM platform 112, such as medical providers (e.g., a medical provider of the person 102) and manufacturers (e.g., a manufacturer of the CGM system 104, the insulin delivery system 106, or the computing device 108) capable of providing medical and manufacturing data, respectively, that can be leveraged by the data analytics platform 122. Certainly, the IoT 114 may include devices and sensors capable of providing a wealth of data for use in connection with glucose prediction using machine learning and glucose measurements without departing from the spirit or scope of the described techniques. In the context of measuring glucose, e.g., continuously, and obtaining data describing such measurements, consider the following description of FIG. 2.

Figure 2:
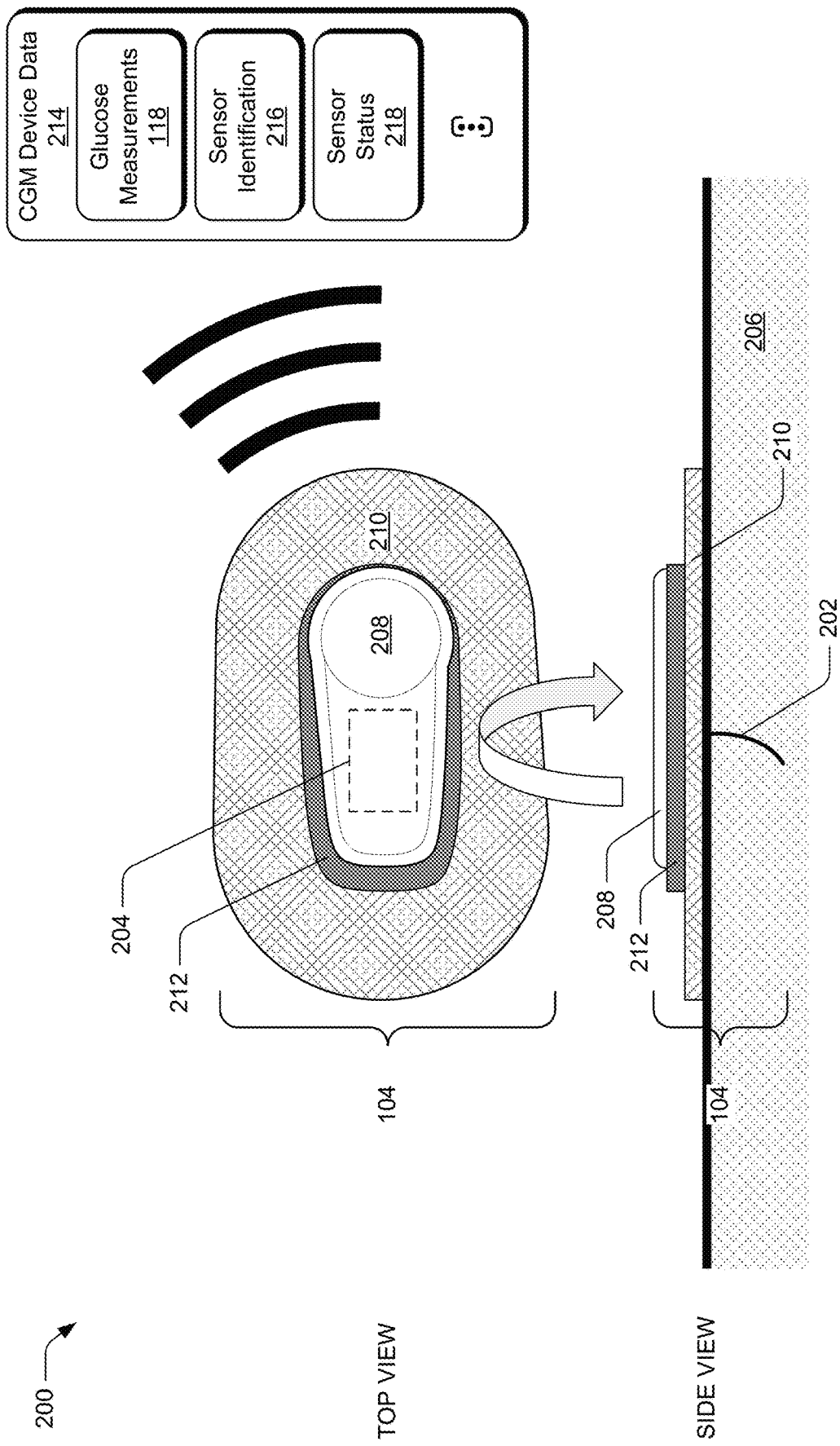
FIG. 2 depicts an example of the continuous glucose monitoring (CGM) system of FIG. 1 in greater detail.

FIG. 2 depicts an example implementation 200 of the CGM system 104 of FIG. 1 in greater detail. In particular, the illustrated example 200 includes a top view and a corresponding side view of the CGM system 104.

The CGM system 104 is illustrated as including a sensor 202 and a sensor module 204. In the illustrated example 200, the sensor 202 is depicted in the side view as inserted subcutaneously into skin 206 (e.g., skin of the person 102). The sensor module 204 is depicted in the top view as a rectangle having a dashed outline. The CGM system 104 is further illustrated as including a transmitter 208. Use of the dashed outline of the rectangle representing sensor module 204 indicates that the sensor module 204 may be housed in, or otherwise implemented within a housing of, the transmitter 208. In this example 200, the CGM system 104 further includes adhesive pad 210 and attachment mechanism 212.

In operation, the sensor 202, the adhesive pad 210, and the attachment mechanism 212 may be assembled to form an application assembly, where the application assembly is configured to be applied to the skin 206 so that the sensor 202 is subcutaneously inserted as depicted. In such scenarios, the transmitter 208 may be attached to the assembly after application to the skin 206, such as via the attachment mechanism 212. Additionally or alternatively, the transmitter 208 may be incorporated as part of the application assembly, such that the sensor 202, the adhesive pad 210, the attachment mechanism 212, and the transmitter 208 (with the sensor module 204) can all be applied to the skin 206 simultaneously. In one or more implementations, the application assembly is applied to the skin 206 using a separate applicator (not shown). This application assembly may also be removed by peeling the adhesive pad 210 off of the skin 206. In this manner, the CGM system 104 and its various components as illustrated in FIG. 2 represent one example form factor, and the CGM system 104 and its components may have different form factors without departing from the spirit or scope of the described techniques.

In operation, the sensor 202 is communicatively coupled to the sensor module 204 via at least one communication channel, which can be a "wireless" connection or a "wired" connection. Communications from the sensor 202 to the sensor module 204, or from the sensor module 204 to the sensor 202, can be implemented actively or passively and may be continuous (e.g., analog) or discrete (e.g., digital).

The sensor 202 may be a device, a molecule, and/or a chemical that changes, or causes a change, in response to an event that is at least partially independent of the sensor 202. The sensor module 204 is implemented to receive indications of changes to the sensor 202, or caused by the sensor 202. For example, the sensor 202 can include glucose oxidase, which reacts with glucose and oxygen to form hydrogen peroxide that is electrochemically detectable by an electrode of the sensor module 204. In this example, the sensor 202 may be configured as, or include, a glucose sensor configured to detect analytes in blood or interstitial fluid that are indicative of glucose level using one or more measurement techniques.

In another example, the sensor 202 (or an additional, not depicted, sensor of the CGM system 104) can include first and second electrical conductors and the sensor module 204 can electrically detect changes in electric potential across the first and second electrical conductors of the sensor 202. In this example, the sensor module 204 and the sensor 202 are configured as a thermocouple, such that the changes in electric potential correspond to temperature changes. In some examples, the sensor module 204 and the sensor 202 are configured to detect a single analyte (e.g., glucose). In other examples, the sensor module 204 and the sensor 202 are configured to detect multiple analytes (e.g., sodium, potassium, carbon dioxide, and glucose). Alternatively or additionally, the CGM system 104 includes multiple sensors to detect not only one or more analytes (e.g., sodium, potassium, carbon dioxide, glucose, and insulin) but also one or more environmental conditions (e.g., temperature). Thus, the sensor module 204 and the sensor 202 (as well as any additional sensors) may detect the presence of one or more analytes, the absence of one or more analytes, and/or changes in one or more environmental conditions.

In one or more implementations, although not depicted in the illustrated example of FIG. 2, the sensor module 204 may include a processor and memory. By leveraging such a processor, the sensor module 204 may generate the glucose measurements 118 based on the communications with the sensor 202 that are indicative of one or more changes (e.g., analyte changes, environmental condition changes, and so forth). Based on communications with the sensor 202, the sensor module 204 is further configured to generate CGM device data 214. CGM device data 214 is representative of a communicable package of data that includes at least one glucose measurement 118. Alternatively or additionally, the CGM device data 214 includes other data, such as multiple glucose measurements 118, sensor identification 216, sensor status 218, combinations thereof, and so forth. In one or more implementations, the CGM device data 214 may include other information, such as one or more of temperatures that correspond to the glucose measurements 118 and measurements of other analytes. In this manner, the CGM device data 214 may include various data in addition to at least one glucose measurement 118, without departing from the spirit or scope of the described techniques.

In operation, the transmitter 208 may transmit the CGM device data 214 wirelessly as a stream of data to the computing device 108. Alternatively or additionally, the sensor module 204 may buffer the CGM device data 214 (e.g., in memory of the sensor module 204) and cause the transmitter 208 to transmit the buffered CGM device data 214 at various intervals, e.g., time intervals (every second, every thirty seconds, every minute, every five minutes, every hour, and so on), storage intervals (when the buffered CGM device data 214 reaches a threshold amount of data or a number of instances of CGM device data 214), combinations thereof, and so forth.

In addition to generating the CGM device data 214 and causing it to be communicated to the computing device 108, the sensor module 204 is configured to perform additional functionality in accordance with one or more implementations. This additional functionality may include generating predictions of future glucose levels for the person 102 and communicating notifications based on the predictions (e.g., notifications of anticipated upcoming events, warnings when predictions indicate that the person 102's glucose levels are likely to be dangerous, and so forth). This computational ability of the sensor module 204 is particularly advantageous where connectivity to services via the network 116 is limited or non-existent. In this way, a person may be alerted to a dangerous condition without having to rely on connectivity (e.g., Internet connectivity). This additional functionality of the sensor module 204 may also include calibrating the sensor 202 initially or on an ongoing basis as well as calibrating any other sensors of the CGM system 104.

With respect to the CGM device data 214, the sensor identification 216 represents information that uniquely identifies the sensor 202 from other sensors (e.g., other sensors of other CGM systems 104, other sensors implanted previously or subsequently in the skin 206, and the like). By uniquely identifying the sensor 202, the sensor identification 216 may also be used to identify other aspects about the sensor 202, such as a manufacturing lot of the sensor 202, packaging details of the sensor 202, shipping details of the sensor 202, and the like. In this way, various issues detected for sensors manufactured, packaged, and/or shipped in a similar manner as the sensor 202 may be identified and used in different ways (e.g., to calibrate the glucose measurements 118, to notify users to change or dispose of defective sensors, to notify manufacturing facilities of machining issues, etc.).

The sensor status 218 represents a state of the sensor 202 at a given time (e.g., a state of the sensor at a same time as one of the glucose measurements 118 is produced). To this end, the sensor status 218 may include an entry for each of the glucose measurements 118, such that there is a one-to-one relationship between the glucose measurements 118 and statuses captured in the sensor status 218 information. Generally, the sensor status 218 describes an operational state of the sensor 202. In one or more implementations, the sensor module 204 may identify one of a number of predetermined operational states for a given glucose measurement 118. The identified operational state may be based on the communications from the sensor 202 and/or characteristics of those communications.

By way of example, the sensor module 204 may include (e.g., in memory or other storage) a lookup table having the predetermined number of operational states and bases for selecting one state from another. For instance, the predetermined states may include a "normal" operation state where the basis for selecting this state may be that the communications from the sensor 202 fall within thresholds indicative of normal operation (e.g., within a threshold of an expected time, within a threshold of expected signal strength, when an environmental temperature is within a threshold of suitable temperatures to continue operation as expected, combinations thereof, and so forth). The predetermined states may also include operational states that indicate one or more characteristics of the sensor 202's communications are outside of normal activity and may result in potential errors in the glucose measurements 118.

For example, bases for these non-normal operational states may include receiving the communications from the sensor 202 outside of a threshold expected time, detecting a signal strength of the sensor 202 outside a threshold of expected signal strength, detecting an environmental temperature outside of suitable temperatures to continue operation as expected, detecting that the person 102 has changed orientation relative to the CGM system 104 (e.g., rolled over in bed), and so forth. The sensor status 218 may indicate a variety of aspects about the sensor 202 and the CGM system 104 without departing from the spirit or scope of the techniques described herein.

Having considered an example environment and example CGM system, consider now a description of some example details of the techniques for generating event predictions and glucose measurement predictions using stacked machine learning models in accordance with one or more implementations.

Glucose Measurement and Event Predictions

Figure 3:
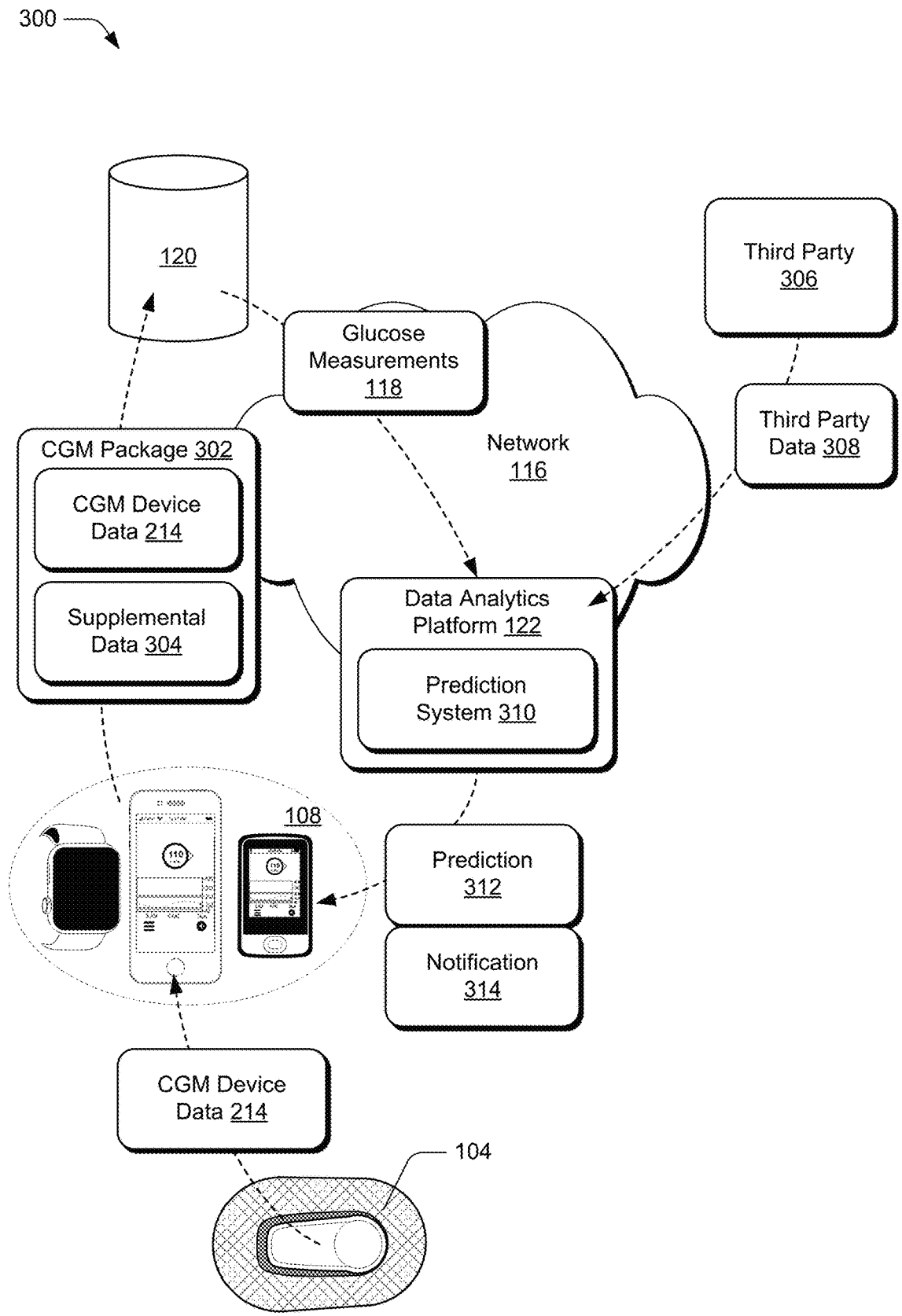
FIG. 3 depicts an example implementation in which CGM device data, including glucose measurements, is routed to different systems in connection with glucose measurement and event predictions.

FIG. 3 depicts an example implementation 300 in which CGM device data, including glucose measurements, is routed to different systems in connection with glucose measurement prediction and event prediction using machine learning.

The illustrated example 300 includes the CGM system 104 and examples of the computing device 108 introduced with respect to FIG. 1. The illustrated example 300 also includes the data analytics platform 122 and the storage device 120, which, as described above, stores the glucose measurements 118. In the example 300, the CGM system 104 is depicted transmitting the CGM device data 214 to the computing device 108. As described with respect to FIG. 2, the CGM device data 214 includes the glucose measurements 118 along with other data. The CGM system 104 may transmit the CGM device data 214 to the computing device 108 in a variety of ways.

The illustrated example 300 also includes CGM package 302. The CGM package 302 may include the CGM device data 214 (e.g., the glucose measurements 118, the sensor identification 216, and the sensor status 218), supplemental data 304, or portions thereof. In this example 300, the CGM package 302 is depicted being routed from the computing device 108 to the storage device 120 of the CGM platform 112. Generally, the computing device 108 includes functionality to generate the supplemental data 304 based, at least in part, on the CGM device data 214. The computing device 108 also includes functionality to package the supplemental data 304 together with the CGM device data 214 to form the CGM package 302 and communicate the CGM package 302 to the CGM platform 112 for storage in the storage device 120 (e.g., via the network 116). Thus, the CGM package 302 may include data collected by the CGM system 104 (e.g., glucose measurements 118 sensed by the sensor 202) as well as supplemental data 304 generated by the computing device 108 that acts as an intermediary between the CGM system 104 and the CGM platform 112, such as a mobile phone or a smart watch of a user.

With respect to the supplemental data 304, the computing device 108 may generate a variety of supplemental data to supplement the CGM device data 214 included in the CGM package 302. In accordance with the described techniques, the supplemental data 304 may describe one or more aspects of a user's context, such that correspondences of the user's context with CGM device data 214 (e.g., the glucose measurements 118) can be identified. By way of example, the supplemental data 304 may describe user interaction with the computing device 108, and include, for instance, data extracted from application logs describing interaction (e.g., selections made, operations performed) for particular applications. The supplemental data 304 may also include clickstream data describing clicks, taps, and presses performed in relation to input/output interfaces of the computing device 108. As another example, the supplemental data 304 may include gaze data describing where a user is looking (e.g., in relation to a display device associated with the computing device 108 or when the user is looking away from the device), voice data describing audible commands and other spoken phrases of the user or other users (e.g., including passively listening to users), device data describing the device (e.g., make, model, operating system and version, camera type, apps the computing device 108 is running), combinations thereof, and so forth.

The supplemental data 304 may also describe other aspects of a user's context, such as environmental aspects including, for example, a location of the user, a temperature at the location (e.g., outdoor generally, proximate the user using temperature sensing functionality), weather at the location, an altitude of the user, barometric pressure, context information obtained in relation to the user via the IoT 114 (e.g., food the user is eating, a manner in which a user is using sporting equipment, clothes the user is wearing), and so forth. The supplemental data 304 may also describe health-related aspects detected about a user including, for example, steps, heart rate, perspiration, a temperature of the user (e.g., as detected by the computing device 108), and so forth. To the extent that the computing device 108 may include functionality to detect, or otherwise measure, some of the same aspects as the CGM system 104, the data from these two sources may be compared for accuracy, fault detection, and so forth. The above-described types of the supplemental data 304 are merely examples and the supplemental data 304 may include more, fewer, or different types of data without departing from the spirit or scope of the techniques described herein.

Regardless of how robustly the supplemental data 304 describes a context of a user, the computing device 108 may communicate the CGM packages 302 (e.g., containing the CGM device data 214 and the supplemental data 304) to the CGM platform 112 for processing at various intervals. In one or more implementations, the computing device 108 may stream the CGM packages 302 to the CGM platform 112 in substantially real-time (e.g., as the CGM system 104 provides the CGM device data 214 continuously to the computing device 108). The computing device 108 may alternatively or additionally communicate one or more of the CGM packages 302 to the CGM platform 112 at a predetermined interval (e.g., every second, every 30 seconds, every hour, and so forth).

Although not depicted in the illustrated example 300, the CGM platform 112 may process CGM packages 302 and cause at least some of the CGM device data 214 and the supplemental data 304 to be stored in the storage device 120. From the storage device 120, this data may be provided to, or otherwise accessed by, the data analytics platform 122, thereby enabling the data analytics platform to generate glucose measurement predictions along with predictions of upcoming events, as described in further detail below.

In one or more implementations, the data analytics platform 122 is configured to ingest data from a third party 306 (e.g., a third party service provider) for use in connection with generating predictions of upcoming glucose levels and upcoming events. By way of example, the third party 306 may produce its own, additional data, such as via devices that the third party 306 manufactures and/or deploys (e.g., exercise equipment, wearable devices, and the like). The illustrated example 300 includes third party data 308, which is shown as being communicated from the third party 306 to the data analytics platform 122 and is representative of additional data produced by, or otherwise communicated from, the third party 306.

As mentioned above, the third party 306 may manufacture and/or deploy associated devices. Additionally or alternatively, the third party 306 may obtain data through other sources, such as corresponding applications. This data may thus include user-entered data entered via corresponding third party applications (e.g., social networking applications, lifestyle applications, and so forth). Given this, data produced by the third party 306 may be configured in various ways, including as proprietary data structures, text files, images obtained via mobile devices of users, formats indicative of text entered to exposed fields or dialog boxes, formats indicative of option selections, combinations thereof, and so forth.

The third party data 308 may describe various aspects related to one or more services provided by a third party without departing from the spirit or scope of the described techniques. The third party data 308 may include, for instance, application interaction data which describes usage or interaction by users with a particular application provided by the third party 306. Generally, the application interaction data enables the data analytics platform 122 to determine usage, or an amount of usage, of a particular application by users of the user population 110. Such data, for example, may include data extracted from application logs describing user interactions with a particular application, clickstream data describing clicks, taps, and presses performed in relation to input/output interfaces of the application, and so forth. In one or more implementations, the data analytics platform 122 is configured to receive the third party data 308 produced, or otherwise obtained, by the third party 306.

The data analytics platform 122 is illustrated as including prediction system 310. In accordance with the described systems, the prediction system 310 is configured to generate predictions 312 based on the glucose measurements 118. Specifically, the prediction system 310 is configured to generate predictions 312 of upcoming glucose measurements and upcoming events over a future time interval, based on glucose measurements 118 obtained during a previous time interval and confidence levels associated with the various predictions 312. For example, the prediction system 310 is configured to predict the occurrence (or lack thereof) of an upcoming event over a time interval based on glucose measurements 118 obtained during a previous time interval, historical user information, and combinations thereof. As described in further detail below, the predictions 312 may be based on glucose measurements 118 that have been sequenced according to timestamps to form time sequenced glucose measurements (e.g., glucose traces). In one or more implementations, for instance, additional data used by the prediction system 310 to generate predictions 312 may include one or more portions of the CGM device data 214, supplemental data 304, third party data 308, data from the IoT 114, combinations thereof, and so forth. As described below, the prediction system 310 may generate such predictions 312 by using multiple machine learning models arranged in a stacked configuration. These models may be trained, or otherwise built, using the glucose measurements 118 and additional data obtained from the user population 110.

Based on the generated predictions 312, the data analytics platform 122 may also generate notifications 314. A notification 314, for instance, may alert a user about an upcoming event prediction, such that the user is likely to eat a meal and be subject to changes in glucose levels responsive to eating the meal (e.g., eating a particular food or drink). Alternatively or additionally, the notification 314 may notify the user that the user is anticipated to administer insulin, be subject to stress, exercise, sleep, and so forth, where each event may be associated with a different anticipated response expressed in glucose levels. The notification 314 may also provide support for deciding how to mitigate adverse health effects associated with problematic glucose levels, such as by recommending the user perform an action (e.g., consume a particular food or drink, download an app to the computing device 108, seek medical attention immediately, decrease insulin dosages, modify exercise behavior), continue a behavior (e.g., continue eating a certain way or exercising a certain way), change a behavior (e.g., change eating habits or exercise habits, change basal or bolus insulin dosages), combinations thereof, and so forth.

In such scenarios, the prediction 312 and/or the notification 314 is communicated from the data analytics platform 122 and output via the computing device 108. In the illustrated example 300, the prediction 312 and the notification 314 are further illustrated as being communicated to the computing device 108. Additionally or alternatively, the prediction 312 and/or the notification 314 may be routed to a decision support platform and/or a validation platform, before the prediction 312 and/or notification 314 are delivered to the computing device 108. In the context of generating predictions 312, consider the following description of FIG. 4.

Figure 4:
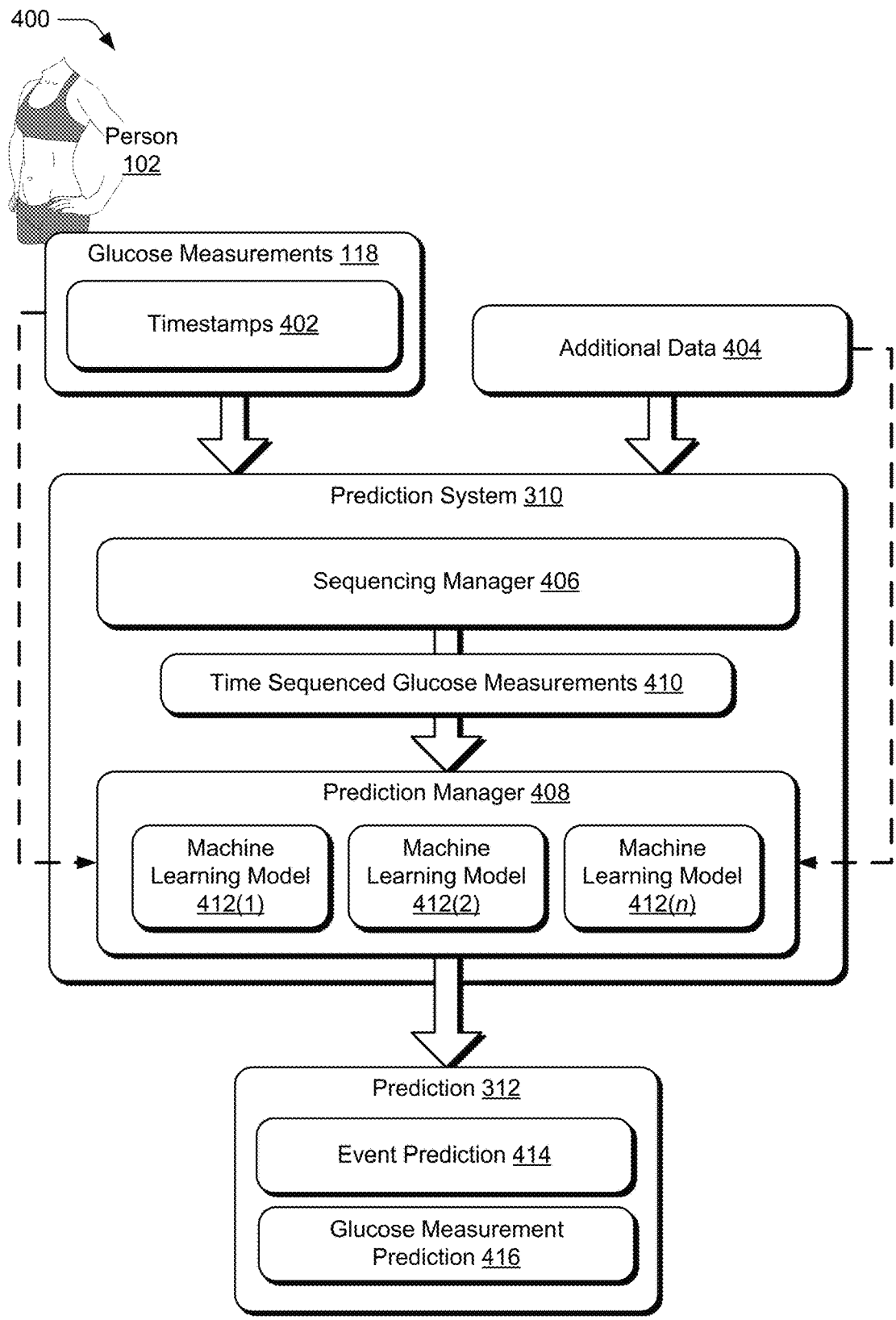
FIG. 4 depicts an example implementation of the prediction system of FIG. 3 in greater detail to generate glucose measurement predictions and event predictions using stacked machine learning models.

FIG. 4 depicts an example implementation 400 of the prediction system 310 of FIG. 3 in greater detail to predict glucose measurements for an upcoming time interval and whether an event will occur during the upcoming time interval, using multiple machine learning models arranged in a stacked configuration.

In the illustrated example 400, the prediction system 310 is configured to receive glucose measurements 118 (e.g., from the storage 120), timestamps 402, and additional data 404. In accordance with one or more implementations, the glucose measurements 118 and the additional data 404 may correspond to the person 102. Each of the glucose measurements 118 corresponds to one of the timestamps 402. In this manner, there may be a one-to-one relationship between glucose measurements 118 and timestamps 402, such that there is a corresponding timestamp 402 for each individual glucose measurement 118. In one or more implementations, the CGM device data 214 may include a glucose measurement 118 and a corresponding timestamp 402. Accordingly, the corresponding timestamp 402 may be associated with the glucose measurement 118 at the CGM system 104 level (e.g., in connection with producing the glucose measurement 118). Regardless of how a timestamp 402 is associated with a glucose measurement 118—or which device associates a timestamp 402 with a glucose measurement 118—each of the glucose measurements 118 has a corresponding timestamp 402.

In this example 400, the prediction system 310 is depicted as including sequence manager 406 and a prediction manager 408, where the prediction manager 408 is configured to generate a prediction 312 based on one or more of the glucose measurements 118, the timestamps 402, and the additional data 404. Although the prediction system 310 is depicted including only the sequencing manager 406 and the prediction manager 408, the prediction system 310 may have more, fewer, and/or different components to generate the prediction 312, examples of which are described in further detail below.

The sequencing manager 406 is representative of functionality of the prediction system 310 to generate time sequenced glucose measurements 410 (e.g., time-series data) based on the glucose measurements 118 and the timestamps 402. Although the glucose measurements 118 may generally be received in sequential order (e.g., by the CGM platform 112 from the CGM system 104 and/or the computing device 108 as glucose measurements 118 are produced), in some instances one or more of the glucose measurements 118 may not be received in a same order in which the glucose measurements 118 are produced (e.g., packets with the glucose measurements 118 may be transmitted or received out of order). Thus, the order of receipt may not chronologically match the order in which the glucose measurements 118 are produced by the CGM system 104. Alternatively or additionally, communications including one or more of the glucose measurements 118 may be corrupted. In this manner, there may be a variety of reasons why the glucose measurements 118, as obtained by the prediction system 310, may not be entirely in time order.

To generate the time sequenced glucose measurements 410, the sequencing manager 406 determines a time-ordered sequence of the glucose measurements 118 according to the respective timestamps 402. The sequencing manger 406 outputs the time-ordered sequence of the glucose measurements 118 as the time sequenced glucose measurements 410. The time sequenced glucose measurements 410 may individually be configured, or otherwise referred to, as a "glucose trace."

In accordance with the techniques described herein, the sequencing manager 406 generates the time sequenced glucose measurements 410 for a specific time interval. In one or more implementations, the time sequenced glucose measurements 410 correspond to a time interval corresponding to previous days, and are utilized by the machine prediction manager 408 to predict whether one or more events will occur during a current or upcoming day, as well as predict glucose measurements throughout the current or upcoming day. Thus, unlike conventional systems which extract features from glucose measurements in order to generate predictions, the time sequenced glucose measurements 410 correspond to an entire set of estimated glucose values for a particular person 102 over any suitable range of previous time periods (e.g., a previous one or more days, a previous 12 hours, a previous 6 hours, a previous 1 hour, a previous 30 minutes, and so forth). Notably, the duration and timing of the time interval over which the time sequenced glucose measurements 410 correspond may vary based on a variety of factors, without departing from the spirit or scope of the techniques described herein. For example, in some cases the time interval may be customized to correspond to the person 102's activity schedule (e.g., using one time interval to correspond to the person 102's sleep schedule and another time interval to correspond to the person 102's active (i.e., awake) schedule. In this manner, the sequencing manager 406 is configured to generate time sequenced glucose measurements 410 for any suitable time interval, which may span multiple days (e.g., the previous seven days), may span certain hours of multiple days (e.g., 5 AM to 10 PM of the previous 14 days), and so forth.

When provided glucose measurements and/or user behavior information as input, the prediction manager 408 is configured to generate the prediction 312. In accordance with one or more implementations, the prediction manager 408 is further configured to generate the prediction 312 by supplementing the input of glucose measurements 118 (e.g., in the form of time sequenced glucose measurements 410) with additional data 404. The additional data 404 is representative of information useable to describe various aspects that may impact future glucose levels of the person 102. The additional data 404 may be correlated in time with glucose measurements 118 (e.g., based on timestamps associated with the additional data 404). Such additional data 404 may include, by way of example and not limitation, application usage data (e.g., clickstream data describing user interfaces displayed and user interactions with applications via the user interfaces), accelerometer data of a mobile device or smart watch (e.g., indicating that that the person has viewed a user interface of the device and thus has likely seen an alert or information related to a predicted event), explicit feedback to notification prompts requesting input on a user's current or planned activities, data describing insulin administered (e.g., timing and insulin doses), data describing food consumed (e.g., timing of food consumption, type of food, and/or amount of carbohydrates consumed), activity data from various sensors (e.g., step data, workouts performed, or other data indicative of user activity or exercise), glucose level responses to stress, combinations thereof and so forth.

In this manner, the additional data 404 may include information describing the occurrence of actual historical events that may influence future glucose measurement predictions. For instance, in an example scenario where the additional data 404 includes information specifying that the person 102 exercised at 4 PM on a Thursday, the additional data 404 may be used as a basis for generating a prediction pertaining to a future time interval, such as for a time interval spanning 12 PM to 1 PM on the following Saturday. Because changes occur in muscles that affect the person 102's sensitivity to insulin for many hours (e.g., 48 hours or more) following exercise, information confirming when the person 102 previously exercised is critical in generating an accurate prediction 312 pertaining to a future insulin administration event. Thus, by considering additional data 404 confirming occurrence of the exercise event, a subsequently generated prediction 312 can be used to recommend a correct dose and/or type of insulin to be administered in a manner that mitigates potential health consequences (e.g., late-onset post-exercise hypoglycaemia).

Further examples of aspects that may be indicative of a person's future glucose levels may include a temperature of the person 102, an environmental temperature, barometric pressure, and the presence or absence of various health conditions (e.g., pregnancy, sickness, etc.). Further still, aspects that may be indicative of a person's future glucose levels may include data describing aspects of exercise (e.g., workout frequency, duration, intensity, and so forth), sleep (e.g., duration, quality, etc.), stress (e.g., blood pressure, heart rate, and the like), to name just a few. In this manner, the additional data 404 may include the supplemental data 304 and/or the third party data 308 described above with reference to FIG. 3. In some implementations, the additional data 404 may be representative of information output by one or more machine learning models implemented by the prediction manager 408 in generating prediction 312.

In order to generate the prediction 312, the prediction manager leverages a plurality of machine learning models 412, arranged in a stacked configuration relative to one another, such that an output from one of the machine learning models 412 can be provided as input to other ones of the machine learning models 412, as illustrated and described in further detail below with respect to FIG. 5. Although illustrated as including only three different machine learning models 412(1), 412(2), and 412(n), the prediction manager 408 is configured to implement any number of n different machine learning models 412, where n is representative of an integer greater than or equal to two. Each machine learning model 412 is representative of a machine learning model trained to process input data, recognize patterns in the input data, and generate a predicted output based on the recognized patterns. Different ones of the machine learning models 412 may be representative of a machine learning model trained according to a different task or objective. For example, machine learning model 412(1) may be trained upon a glucose measurement prediction objective for the person 102, when provided one or more of the additional data 404, the glucose measurements 118, or outputs from one or more other machine learning models 412 implemented by the prediction manager 408. Other ones of the machine learning models, such as machine learning model 412(2) and 412(n) may be trained upon different event prediction objectives, such as to individually predict one of an insulin administration event, an exercise event, a meal event, a sleep or other recovery event, a stress event, and so forth.

Each of the plurality of machine learning models 412, in addition to being trained on information that is particular to the person 102, may further be trained using historical additional data of the user population. In this manner, an accuracy and confidence associated with predictions generated by each of the machine learning models 412 are increased by utilizing the glucose measurements 118, the additional data 404, and predictions generated by other machine learning models 412 of the stacked configuration to generate the prediction for which the machine learning model 412 was trained.

In one or more implementations, the additional data 404 received as input by the prediction manager 408 is associated with an application of the CGM platform 112. For example, an application of the CGM platform 112 may be executed at a user's computing device (e.g., a smartphone or smartwatch) to display the glucose measurements 118 to the user (e.g., in a user interface of an application of the CGM platform). In this manner, the additional data 404 may correspond to screen views or user selections of different controls of the CGM application. Such application usage data enables the prediction manager 408 to receive feedback from a user regarding whether an event prediction 414 included as part of the prediction 312 is accurate (e.g., whether the event indicated by the event prediction 414 is upcoming, actively ongoing, or incorrect). This feedback may be used to assign a confidence level associated with an event prediction 414, which may further be used by the prediction system 310 to selectively provide prediction information output by one of the machine learning models 412 to one or more other machine learning models arranged in the stacked configuration. As such, individual machine learning models 412 of the prediction manager 408 can learn patterns associated with various event responses (e.g., glucose level changes) pertaining to the person 102, and then adjust their respective predictions accordingly.

Generally, the event prediction 414 output by the prediction manager 408 is representative of a prediction of whether a particular type of event will occur for the person during a time interval for which the glucose measurement prediction 416 is to be generated (e.g., a time interval subsequent to a time interval defined by the time sequenced glucose measurements 410). The glucose measurement prediction 416 may be representative of an output prediction generated by one of the stacked machine learning models 412 of the prediction manager 408, which in turn may be trained, or an underlying model may be learned, based on one or more training approaches and using one or more of historical glucose measurements 118, additional data 404, or output predictions generated by other ones of the stacked machine learning models 412.

The glucose measurement predictions 416 output by one of the machine learning models 412 may be provided as input to one or more of the other machine learning models 412 to generate the event prediction 414. For instance, a machine learning model 412 trained to generate an event prediction 412 may be configured to identify a pattern in the glucose measurement prediction 416 that correlates to historical information for the person 102, such as a pattern of glucose level changes that correspond to glucose level changes associated with the person 102's response to exercise, response to eating a meal, response to stress, response to insulin administration, response to sleep, combinations thereof, and so forth. By leveraging the stacked configuration of machine learning models 412 implemented by the prediction manager 408, event predictions 414 and glucose measurement predictions 416 may each be representative of additional data 404 provided to the prediction system 310 in training various machine learning models 412 and generating the prediction 312. Training of individual ones of the machine learning models 412 is described in further detail below with respect to FIG. 12.

Each machine learning model 412 implemented in the stacked configuration by prediction manager 408 may be implemented in a variety of different ways without departing from the spirit or scope of the described techniques. Each machine learning model 412, for instance, may receive as input labeled streams of observed glucose values collected over an interval of time to produce an anticipated output. The streams of estimated glucose values are labeled to indicate whether or not a particular event occurred during the particular interval of time, along with timestamps defining a start and end of the particular event, as well as glucose levels and changes thereof preceding the particular event, during the particular event, and following the particular event. In this manner, each machine learning model may be configured as a single model or an ensemble of models that includes multiple models. Example machine learning models may include, for instance, neural networks (e.g., recurrent neural networks such as long-short term memory (LSTM)), state machines, Markov chains, Monte Carlo methods, and particle filters, to name just a few. Thus, the stack of machine learning models 412 are configured to classify input streams of observed glucose values and contextual data describing various influences upon the observed glucose values in order to generate glucose measurement predictions and events associated therewith.

Figure 5:
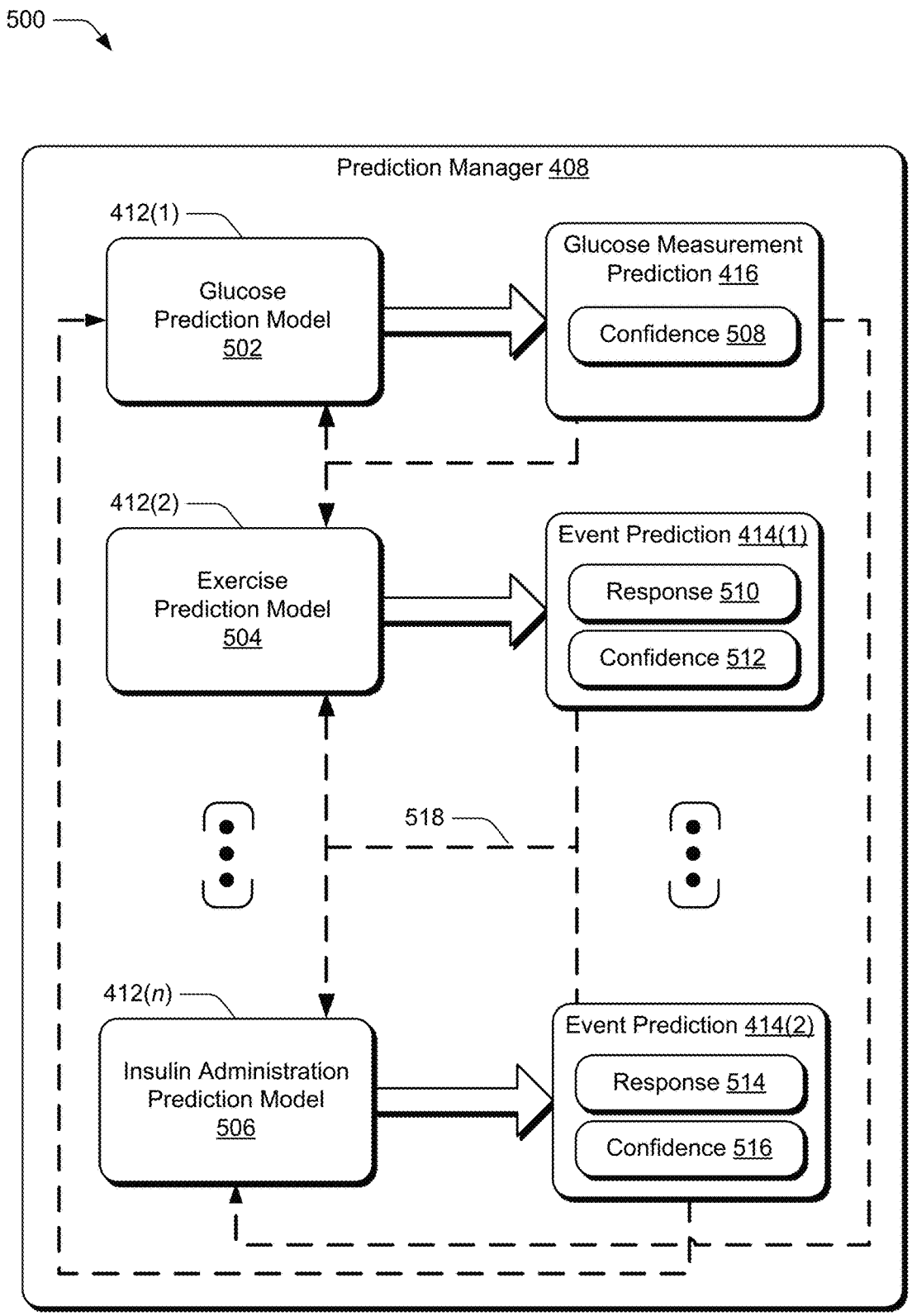
FIG. 5 depicts an example implementation of stacked machine learning models implemented by the prediction system of FIG. 3 in accordance with one or more implementations.

Consider, for example, FIG. 5 which depicts an example implementation 500 of multiple machine learning models arranged in a stacked configuration that may be implemented by the prediction manager to generate one or more of an event prediction or a glucose measurement prediction in accordance with one or more implementations. In the illustrated example 500, the prediction manager 408 includes machine learning models 412(1), 412(2), and 412(n), as illustrated and introduced with respect to FIG. 4. In the illustrated example 500, machine learning model 412(1) is configured as glucose prediction model 502, configured to output glucose measurement prediction 416 when provided with one or more of the glucose measurements 118 or additional data 404 as inputs. Machine learning model 412(2) is configured as exercise prediction model 504, configured to output event prediction 414(1) (e.g., an upcoming exercise event) when provided with one or more of the glucose measurements 118 or additional data 404 as inputs. Machine learning model 412(n) is configured as insulin administration model 506, configured to output event prediction 414(2) (e.g., an upcoming insulin administration event) when provided with one or more of the glucose measurements 118 or additional data 404 as inputs. Although only illustrated as implementing three different machine learning models, the prediction manager 408 is configured to implement any number of multiple machine learning models to generate a prediction 312, as indicated by the ellipses separating models 412(2) and 412(n), and their corresponding predictions 414(1) and 414(2). Also, in cases where the stack includes three models, the three models of the stack may be a different combination of models than illustrated and discussed below.

In any case, each output generated by the machine learning models 412(1), 412(2), and 412(n) may further be associated with a confidence value for the output prediction. In instances where the predicted output generated by a machine learning model 412 corresponds to an event prediction 414, the event prediction 414 may specify both a confidence value associated with the event prediction as well as an anticipated response associated with the particular event, such as an anticipated change in glucose levels for the person 102 leading up to, during, and following the particular event. For instance, the glucose measurement prediction 416 is illustrated as having an associated confidence 508, which is representative of a score or value indicating a probability that the glucose measurement prediction 416 will align with future, actual glucose measurements for a particular user (e.g., future glucose measurements 118 for person 102). Similarly, event predictions 414(1) and 414(2) are each output as having associated confidence values 512 and 516, respectively indicating whether a corresponding event will occur during the time step for which the glucose measurement prediction 416 is generated.

A confidence value associated with an output prediction may be represented as a value between zero and one, inclusive, where zero indicates that the output prediction is inaccurate and one indicates that the prediction is accurate. In addition to specifying confidence values 512 and 516, machine learning models 412(2) and 412(n) may be configured to describe anticipated responses 510 and 514, respectively associated with event predictions 414(1) and 414(2). Each anticipated response 510 and 514 includes information useable to describe a response (e.g., change in glucose levels) associated with the corresponding event.

For instance, in the illustrated example 500, response 510 may be indicative of an anticipated drop in glucose levels that occurs as a result of an exercise activity. Similarly, response 514 may be indicative of an anticipated increase in glucose levels that occurs as a result of an insulin administration event. Responses 510 and 514 may be based on aggregated information for various different users of a user population, such as user population 110, may be tailored for a specific user, such as person 102, or combinations thereof. In this manner, the responses 510 and 514 may include specific values describing anticipated effects on the glucose measurement prediction 416 generated for the person 102, accounting for the occurrence, or lack thereof, of one or more specific events.

The responses 510 and 514 may further specify anticipated timing associated with the respective event effects on future glucose measurements. For example, response 510 may include information specifying that the person 102's glucose levels will begin to drop ten minutes after the exercise activity commences until a first level, and remain around (e.g., within 5% difference of) the first level for 11 hours following completion of the exercise activity. Continuing this example, response 514 may include information specifying that the person 102's glucose levels will begin to drop five minutes after occurrence of the insulin administration event at a first rate until the glucose levels reach a second level, approximately two hours after completion of the insulin administration event. Response 514 may further specify that the glucose levels are likely to remain at the second level until approximately four hours after the insulin administration event, at which point the glucose levels are likely to increase at a second rate until they reach a third level approximately five to eight hours following completion of the insulin administration event. Thus, a response associated with an event prediction 414 (e.g., responses 510 and 514) is representative of any range of information describing when and how an individual's glucose levels are anticipated to be affected by a corresponding event.

Recognizing that the associated response of an event prediction 414 may impact the glucose measurement prediction 416 as well as other event predictions 414 output by the various machine learning models 412, and that the glucose measurement prediction 416 in turn may impact the event predictions 414, the prediction manager is configured to selectively provide outputs of one or more of the machine learning models 412 to different ones of the machine learning models 412 (e.g., as additional data 404). This ability to provide outputs of one machine learning model 412 to other machine learning models 412 implemented by the prediction manager 408 is enabled by virtue of their stacked configuration, and represented by the feedback loops 518, illustrated as dashed arrows in the illustrated example of FIG. 5.

In accordance with one or more implementations, the prediction manager 408 selectively filters which outputs of the various machine learning models 412(1), 412(2), and 412(n) are provided as inputs to the machine learning models. This selective filtration may be based at least in part on the confidence level (e.g., confidence level 508, 512, or 516) associated with a particular output, so as to avoid negatively impacting an output accuracy of one or more of the machine learning models 412. For instance, the prediction manager 408 may provide one or more of the glucose measurement prediction 416 or the event predictions 414(1) and 414(2) as input to the machine learning models 412 only if the corresponding output prediction is likely to happen (e.g., having an associated confidence 508, 512, or 516 that satisfies a confidence threshold, such as a 90% or greater confidence). Alternately or additionally, the confidences 508, 512, 516 may be used to weight an influence of the glucose measurement prediction 416 or the event predictions 414(1) and 414(2), when input to a downstream model. By providing selective output predictions for a particular time step or relying less on less accurate predictions (according to the confidences), the prediction manager 408 is configured to improve an accuracy of output predictions for one or more of the stacked machine learning models 412.

For instance, consider an example scenario where the glucose prediction model 502 generates a glucose measurement prediction 416 having a high confidence 508 (e.g., 95% confidence). In response to determining that the confidence 508 satisfies a confidence threshold (e.g., 90% confidence), the prediction manager 408 is configured to provide the glucose measurement prediction 416 for a particular time step to the exercise prediction model 504 as well as the insulin administration prediction model 506. Using the glucose measurement prediction 416 as input, the exercise prediction model 504 may recognize that the glucose measurement prediction 416 corresponds to an event profile (e.g., a pattern of glucose measurements) indicating that the user will likely be exercising during the time step and output event prediction 414(1) indicating that the user will be subject to an exercise event during the time step. The response 510 may thus be indicative of an anticipated change in glucose levels, or other type of response, expected to result from the exercise event.

The confidence 512 represents a degree of certainty that the exercise event will occur during the time step for which the glucose measurement prediction 416 was generated, and may be influenced by the glucose measurement prediction 416 along with one or more additional factors. For instance, additional data 404 provided as input to the exercise prediction model 504 may indicate that the particular user historically exercises from 4 PM to 5 PM on weekdays, and indicate that the time step for which the glucose measurement prediction 416 is generated begins at 4 PM on a Wednesday. Further, the exercise prediction model 504 may identify that one or more values of the glucose measurement prediction 416 correlate with glucose values of an exercise event profile for the particular user. Based on this example information, the confidence 512 may indicate that the particular user is highly likely (e.g., 96% likely) to be exercising during the time step for which the glucose measurement prediction 416 was generated.

In turn, responsive to determining that the confidence 512 for the exercise event prediction 414(1) satisfies a confidence threshold, the response 510 may be provided as feedback to one or more of the stacked machine learning models 412 for use in generating their respective predictions 416, 414(1), and 414(2). For instance, the response 510 may be provided as input to the glucose prediction model 502 for generating a subsequent glucose measurement prediction 416, which may leverage historical information describing the particular user's glucose levels following a workout. Similarly, the response 510 may be leveraged by the insulin administration prediction model 506 to identify that the particular user is unlikely to be administering insulin while exercising, and thereby mitigate a confidence 516 for an insulin administration event prediction that otherwise might result without knowledge that the user is likely to be exercising during the time step for which the event prediction 414(2) is generated.

Having considered an example stacked configuration of machine learning models, consider now example implementations of specific inputs provided to, and outputs generated by, a pipeline of stacked machine learning models implemented by the prediction manager 408 in accordance with the techniques described herein.

Figure 6:
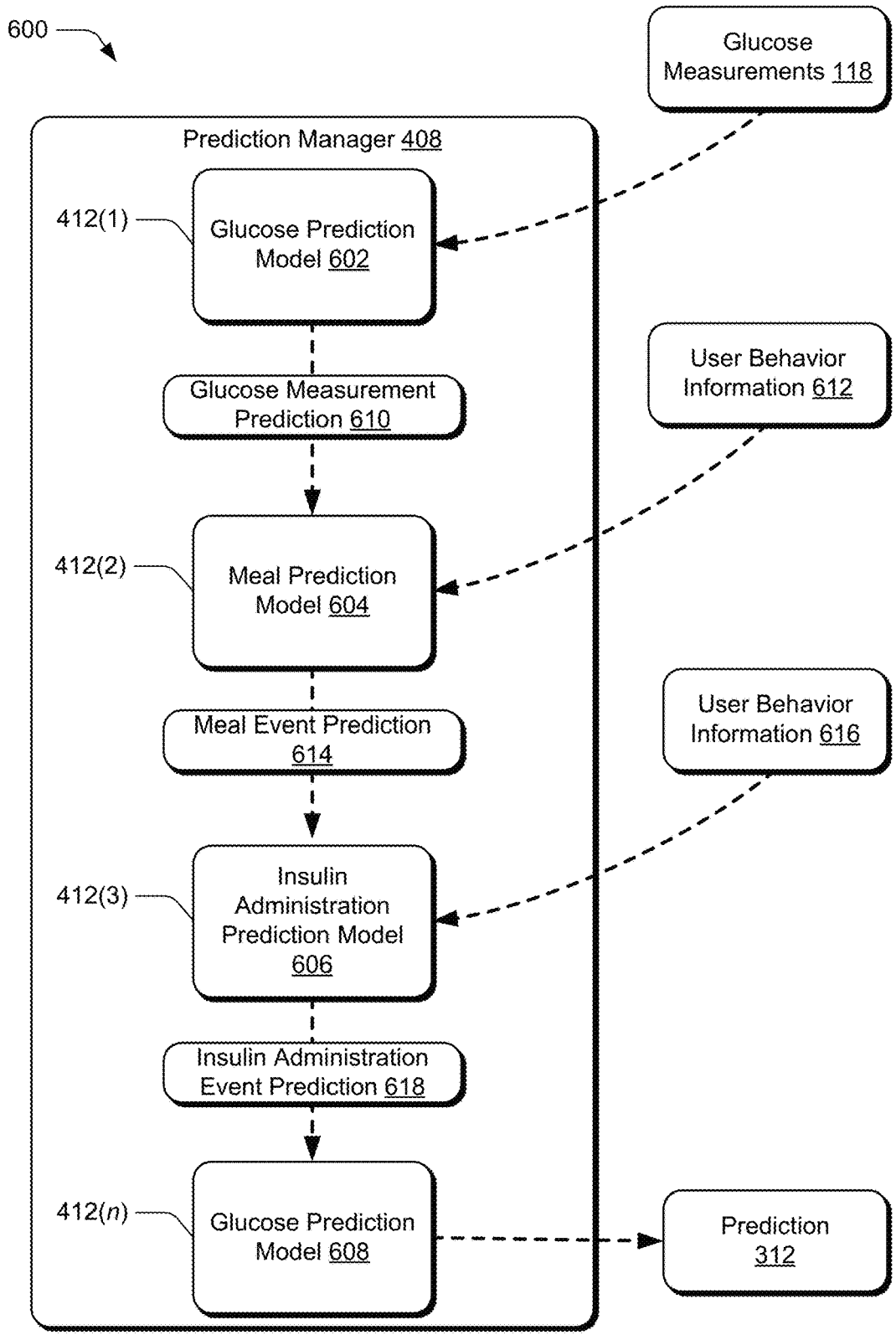
FIG. 6 depicts an example implementation of stacked machine learning models implemented by the prediction system of FIG. 3 in accordance with one or more implementations.

FIG. 6 depicts an example implementation 600 of multiple machine learning models 412(1)-412(n) arranged in a stacked configuration that may be implemented by the prediction manager 408 to generate at least one of an event prediction or a glucose measurement prediction. In the illustrated example 600, the prediction manager 408 includes machine learning models 412(1), 412(2), 412(3), and 412(n), which are representative of various machine learning models that may be implemented by the prediction manager 408, as introduced and described above with respect to FIG. 4. Specifically, in the illustrated example 600, machine learning model 412(1) is configured as glucose prediction model 602, machine learning model 412(2) is configured as meal prediction model 604, machine learning model 412(3) is configured as insulin administration prediction model 606, and machine learning model 412(n) is configured as glucose prediction model 608.

Glucose prediction model 602 is representative of functionality of the prediction manager 408 to generate and output glucose measurement prediction 610 based on one or more inputs, such as based on glucose measurements 118. Alternatively or additionally, although not illustrated in the example 600, glucose prediction model 602 may be configured to generate glucose measurement prediction 610 based on input data other than the glucose measurements 118, such as based on additional data 404. The glucose measurement prediction 610 is thus representative of an instance of glucose measurement 416 introduced with respect to FIG. 4, and a particular manner in which the glucose measurement prediction 610 may be generated by the glucose prediction model 602 is described in further detail below with respect to FIG. 8.

Being configured in a stacked configuration, the glucose measurement prediction 610 output by the glucose prediction model 602 may be provided as input to the meal prediction model 604 for use in generating its respective output. In addition to receiving the glucose measurement prediction 610 as input, the meal prediction model 604 is further configured to receive additional information 404, illustrated in the example 600 as user behavior information 612. User behavior information 612 is thus representative of any suitable type and/or format of information that the meal prediction model 604 is trained to process in generating its output meal event prediction 614, which is representative of an instance of an event prediction 414.

For instance, user behavior information 612 may specific a historical meal schedule of a particular user for which the prediction 312 is generated (e.g., information specifying that the person 102 generally eats lunch at 11:30 AM on weekdays and at 1:00 PM on weekends, information specifying average caloric intake values for the person 102 at various times of the day, and so forth). Alternatively or additionally, user behavior information 612 may specify location information for the particular user that correlates to a pattern identifiable by the meal prediction model 604 to indicate that the particular user is likely to eat during an upcoming time interval (e.g., information indicating that person 102 is currently at a restaurant, information indicating that person 102 has departed from a grocery store, and so forth). Alternatively or additionally, user behavior information 612 may comprise data associated with one or more third-party applications (e.g., an image of a meal uploaded to a social media account of the person 102, placement of an order through a food delivery service, restaurant reservation information saved to a calendar, and the like). In this manner, user behavior information 612 is not so limited to the above-described examples and is representative of any suitable type and/or format of information that may be processed as input by the meal prediction model 604 to generate its respective event prediction 414 (e.g., meal event prediction 614).

The glucose measurement prediction 610 and/or the user behavior information 612 may be received as input by the meal prediction model 604 in any suitable manner, such as input via a multi-feature vector generated by the prediction manager 408, where at least one vector feature represents the glucose measurement prediction 610 and at least one vector feature represents the user behavior information 612. In implementations, one or more of the glucose measurement prediction 610 or the user behavior information 612 may be received by the prediction manager 408 as a data type/format different from a data type/format upon which the meal prediction model 604 was trained. In such implementations, the prediction manager 408 is further configured to process data to be provided as input to the meal prediction model 604, such as to configure the data to a data type/format for which the meal prediction model 604 was trained to generate reliable outputs. In this manner, the meal prediction model 604 is configured to leverage both glucose measurement prediction 610 and user behavior information 612 to make an informed prediction as to whether a user is likely to experience a meal event (e.g., whether the user is likely to eat during an upcoming time interval, an expected caloric intake associated with the meal, an anticipated glucose level response associated with the meal event, combinations thereof, and so forth).

The meal event prediction 614 and its associated information (e.g., confidence score, anticipated glucose level response, and so forth) may subsequently be provided as input to insulin administration prediction model 606 for use in generating its respective output. In addition to receiving the meal event prediction 614 as input, the insulin administration prediction model 606 may be configured to receive user behavior information 616, which is representative of an instance of additional data 404. User behavior information 616 is thus representative of any suitable type and/or format of information that the insulin administration prediction model 606 is trained to process in generating and outputting insulin administration event prediction 618, which is representative of an instance of an event prediction 414.

For instance, user behavior information 616 may describe an insulin administration schedule for the particular user for which the prediction 312 is generated (e.g., information specifying a type of insulin generally administered by person 102, information specifying a normal time prior to eating at which the person 102 administers insulin, and so forth). Alternatively or additionally, user behavior information 616 may be representative of information provided by insulin delivery system 106 (e.g., information describing insulin administration events over a past time period, information describing a particular dose of insulin, and so forth). Alternatively or additionally, user behavior information 616 may describe how a particular dose of insulin affects the person 102's glucose levels (e.g., information describing glucose level responses based on different insulin types and/or administration quantities). In this manner, user behavior information 616 is not so limited to the above-described examples and is representative of any suitable information that may be processed as input by the insulin administration prediction model 606 to generate its respective insulin administration prediction model 606 to generate the insulin administration event prediction 618.

One or both of the meal event prediction 614 and the user behavior information 616 may be received as input by the insulin administration prediction model 606 in any suitable manner, such as input via a multi-feature vector generated by the prediction manager 408, where at least one vector feature represents meal event prediction 614 and at least one vector feature represents user behavior information 616. In implementations, one or more of the meal event prediction 614 or the user behavior information 616 may be received by the prediction manager 408 as a data type/format different from a data type-format upon which the insulin administration prediction model 606 was trained to generate reliable outputs. In such implementations, the prediction manager 408 is further configured to process data to be provided as input to the insulin administration prediction model 606, such as to configure information to an appropriate data type/format for the insulin administration prediction model 606. In this manner, the insulin administration prediction model 606, by virtue of arrangement in a stacked configuration with other machine learning models, is configured to leverage information described in one or more of the glucose measurements 118, glucose measurement prediction 610, user behavior information 612, meal event prediction 614, or user behavior information 616 in predicting whether an insulin administration event will occur during an upcoming time interval. The insulin administration event prediction 618 is thus representative of an indication as to whether insulin administration will occur, a confidence associated with the insulin administration, an anticipated glucose response associated with the insulin administration, combinations thereof, and so forth.

The insulin administration event prediction 618 output by the insulin administration model 606 can then be provided as input to the glucose prediction model 608, which represents a furthest "downstream" model in the computational flow of generating prediction 312 using the stacked machine learning models 412(1)-(n). In the illustrated example 600, the glucose prediction model 608 represents functionality of the prediction manager 408 to generate prediction 312, which may include glucose measurement prediction 416. In this manner, the glucose measurement prediction specified by prediction 312 represents an instance of glucose measurement prediction 610 having increased accuracy by way of considering contextual information beyond the glucose measurements 118 (e.g., by considering user behaviors information 612 and 616 and information specified by meal and insulin administration predictions 614 and 618). Thus, prediction 312 may be representative of a glucose measurement 416 that more accurately reflects a particular user's glucose levels over a future time step by considering the likelihood of one or more events occurring during the future time step.

Although functionality of the prediction manager 408 has thus far been described with respect to initially receiving glucose measurements, using the glucose measurements to generate a glucose measurement prediction, and using the glucose measurement prediction as input to one or more downstream machine learning models arranged in a stacked configuration, the techniques described herein are not so limited. For instance, in some implementations, an initial input to the stacked machine learning models 412(1)-(n) may be information not explicitly described by glucose measurements 118, such as user behavior information represented herein as additional data 404. In some implementations, the stacked machine learning models 412(1)-(n) may exclude glucose prediction model 602, such that a flow of operations performed by the stacked machine learning models 412(1)-(n) does not begin with generating a glucose measurement prediction. For instance, consider the illustrated example of FIG. 7.

Figure 7:
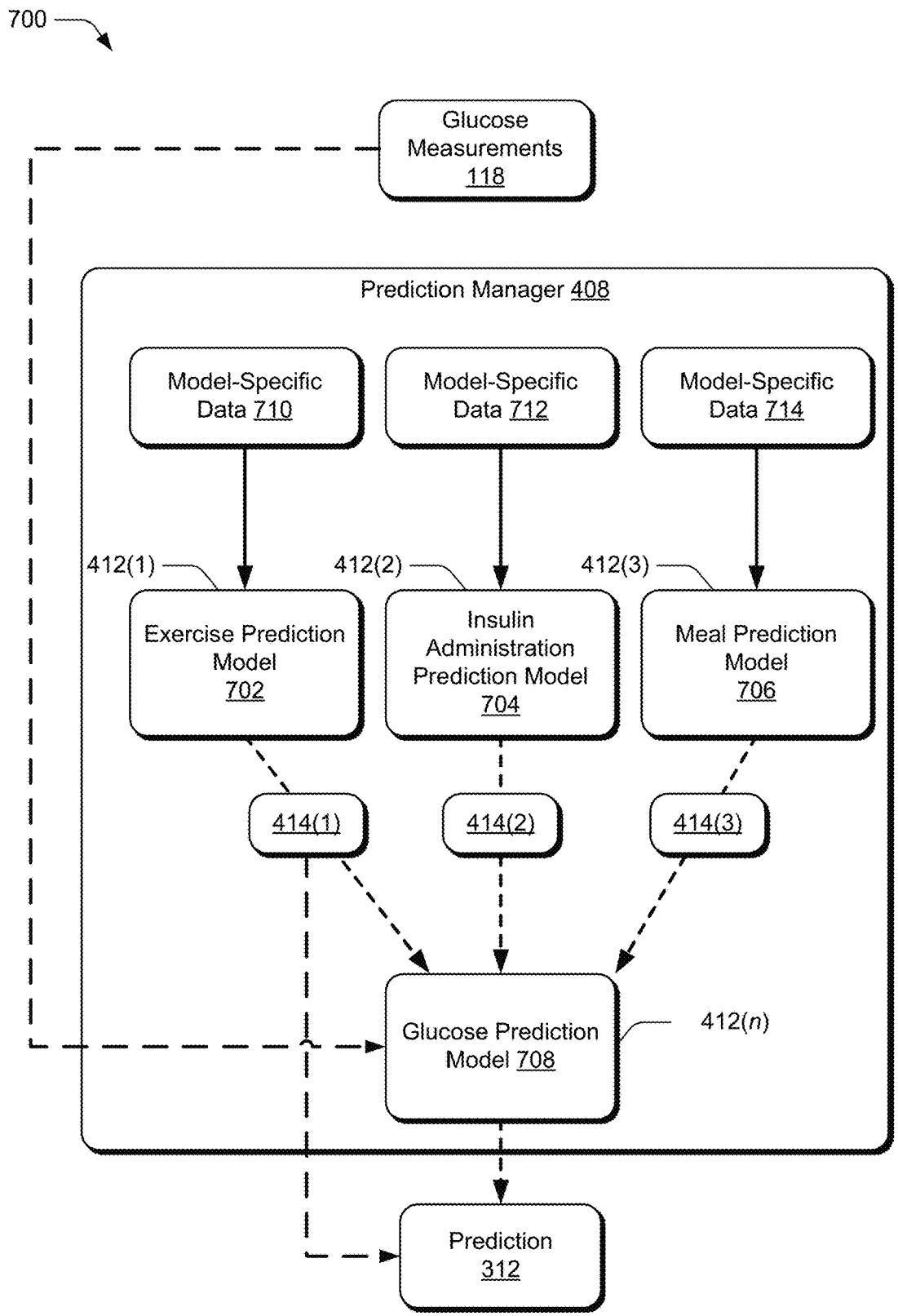
FIG. 7 depicts an example implementation of stacked machine learning models implemented by the prediction system of FIG. 3 in accordance with one or more implementations.

FIG. 7 depicts an example implementation 700 of multiple machine learning models 412(1)-412(n) arranged in a stacked configuration that may be implemented by the prediction manager 408 to generate at least one of an event prediction or a glucose measurement prediction. In the illustrated example 700, the prediction manager 408 includes machine learning models 412(1), 412(2), 412(3), and 412(n), which are representative of various machine learning models that may be implemented by the prediction manager 408, as introduced and described above with respect to FIG. 4. Specifically, in the illustrated example 700, machine learning model 412(1) is configured as exercise prediction model 702, machine learning model 412(2) is configured as insulin administration prediction model 704, machine learning model 412(3) is configured as meal prediction model 706, and machine learning model 412(n) is configured as glucose prediction model 708.

Exercise prediction model 702 is representative of functionality of the prediction manager 408 to process model-specific data 710, which may be representative of one or more instances of additional data 404 and/or glucose measurements 118, and generate event prediction 414(1). In the context of the illustrated example 700, event prediction 414(1) may correspond to a prediction of whether a particular user will exercise during a future time interval and may further include information specifying a confidence level associated with the prediction, an anticipated response of the particular user to the exercise, and so forth.

Insulin administration prediction model 704 is representative of functionality of the prediction manager 408 to process model-specific data 712, which may be representative of one or more instances of additional data 404 and/or glucose measurements 118, and generate event prediction 414(2). In the context of example 700, event prediction 414(2) may correspond to a prediction of whether the particular user will administer insulin during the future time interval (and in some cases a type, how much, and a time over which it is administered), specify a confidence level associated with the insulin administration prediction, specify an anticipated glucose level response of the particular user to the insulin administration, and so forth.

Meal prediction model 706 is representative of functionality of the prediction manager 408 to process model-specific data 714, which may be representative of glucose measurements 118 and/or one or more instances of additional data 404, and generate event prediction 414(3). In the context of example 700, event prediction 414(3) may correspond to a prediction of whether the particular user will eat during the future time interval, specify a confidence level associated with the meal event prediction, specify an anticipated glucose level response of the particular user to eating, and so forth.

In this manner, the instances of model-specific data 710, 712, and 714 are representative of any information describing a user's behavior that may not be explicitly reflected in the glucose measurements 118. Specific attributes or characteristics of various instances of model-specific data 710, 712, and 714 thus depend on a data type and/or data format upon which the corresponding machine learning model 412(1), 412(2), or 412(3) is trained to generate its respective event prediction 414(1), 414(2), or 414(3).

One or more of the event predictions 414(1), 414(2), or 414(3) may then be provided to glucose prediction model 708 for use in generating prediction 312. A determination of whether to provide the event predictions 414(1), 414(2), and 414(3) as input to the glucose prediction model 708 may depend on a respective confidence score and respective confidence threshold value(s) associated with the event prediction. In this manner, the glucose prediction model 708 is provided with information output by at least one other machine learning model arranged in the stacked configuration only when that information is deemed to be reliable. In implementations where the prediction 312 is representative of a glucose measurement prediction 416, the glucose prediction model 708 may supplement the input of one or more of the event predictions 414(1), 414(2), or 414(3) with glucose measurements 118, such that the prediction 312 is representative of a more accurate glucose measurement prediction in comparison to one generated without considering contextual information beyond the glucose measurements 118.

Alternatively or additionally, the prediction 312 may be representative of an event prediction, such as one or more of the event predictions 414(1), 414(2), or 414(3) output by exercise prediction model 702, insulin administration prediction model 704, or meal prediction model 706, as indicated by the arrow connecting event prediction 414(1) to prediction 312. In this manner, the prediction 312 is representative of information useable by the prediction system 310 to be better informed of a user's health and wellbeing, in contrast to conventional systems that disregard information beyond historical glucose measurements or fail to account for the occurrence of events that may impact the user's future glucose levels, as represented herein by the consideration of additional data 404.

Figure 8:
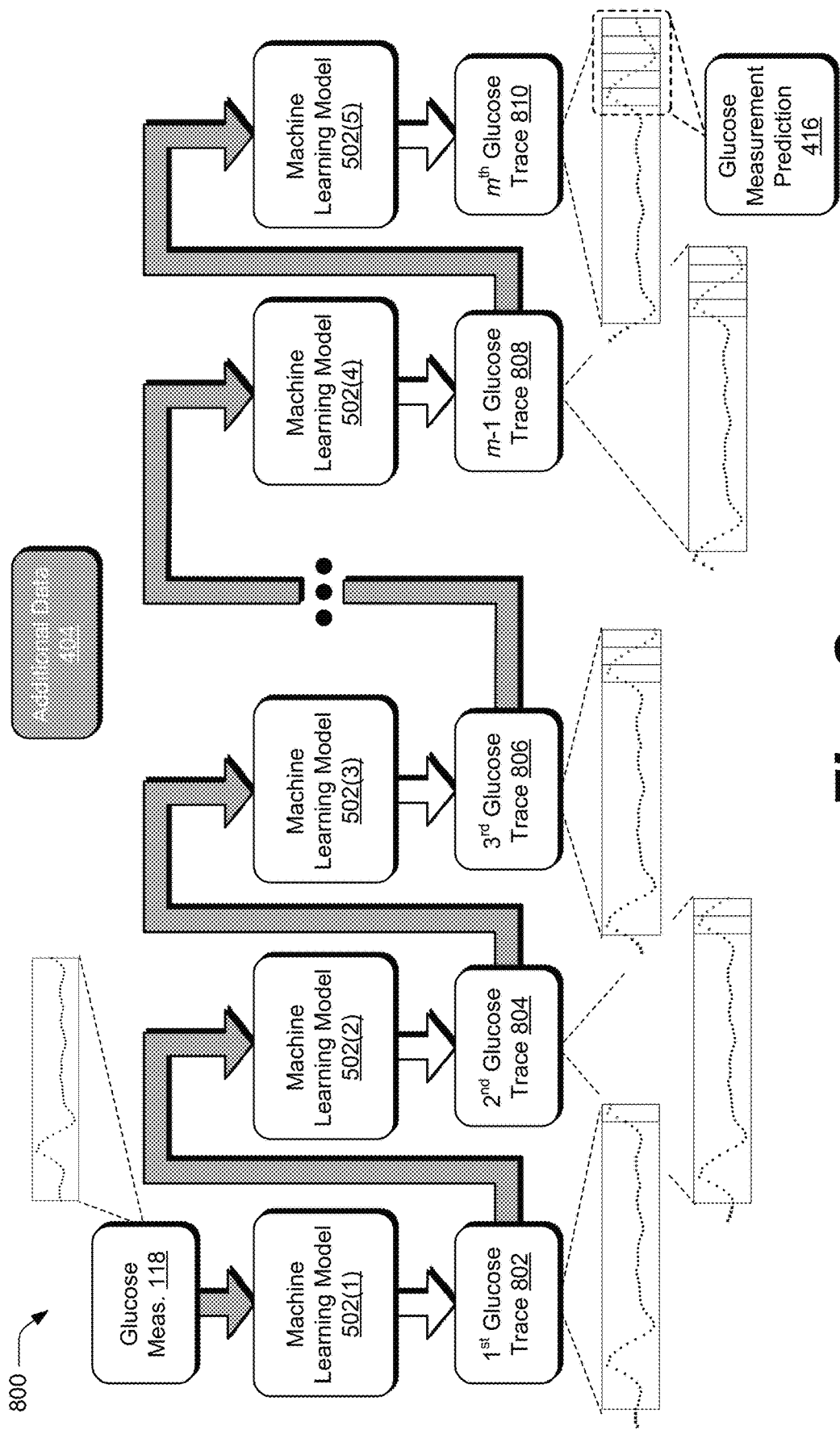
FIG. 8 depicts an additional example implementation in which one of the stacked machine learning models implemented by the prediction system of FIG. 3 generates glucose measurement predictions in accordance with one or more implementations.

For a more detailed example of how a machine learning model 412 generates a prediction based on glucose measurements 118 and/or additional data 404, consider now FIG. 8.

FIG. 8 depicts an example implementation 800 in which one of the stacked machine learning models implemented by the prediction system of FIG. 3 generates glucose measurement predictions 416 based on glucose measurements 118.

The illustrated example 800 includes the glucose measurements 118 and the glucose measurement predictions 416. The glucose measurements 118 are depicted as input to, and the glucose measurement prediction 416 is depicted as output from, steps of one of the machine learning models 412 implemented by the model manager 408, such as glucose prediction model 502. Various steps of the glucose prediction model 502 are represented as 502(1)-(5), which may represent a scenario where the glucose prediction model 502 is configured as a recurrent neural network, such as an LSTM network. When configured as a LSTM network, the steps of the machine learning model 502(1)-(5) may represent repeating modules of the network.

The illustrated example 800 further depicts glucose traces 802-810, including a first glucose trace 802, a second glucose trace 804, a third glucose trace 806, a $(m-1)^{th}$ glucose trace 808, and a $m^{th}$ glucose trace 810. Each glucose trace 802-810 includes a visualization of glucose information represented by the respective trace, representing how sequential steps of the machine learning model 502 are used to predict discrete segments of an upcoming time step for which the glucose measurement prediction 416 is generated. In this manner, the glucose measurements 118 includes a plurality of points representing observed glucose measurements, such as observed glucose measurements 118 for person 102. When provided with the glucose measurements 118, or time sequenced glucose measurements 410, as input, the machine learning model 502(1) generates one or more predicted glucose measurements for the person 102 to occur following an ending timestamp 402 associated with the glucose measurements 118.

The glucose measurements 118 together with the one or more predicted glucose measurements are then combined to form first glucose trace 802, which in turn is provided as input to machine learning model 502(5) to generate its predicted output (e.g., second glucose trace 804). This process continues, with the second glucose trace 804, which maintains the observed glucose measurements described by the glucose measurements 118 and the predicted glucose measurements described by the first glucose trace 802, provided as input to the machine learning model 502(3) to generate the third glucose trace 806. In this manner, additional predicted glucose measurement information is provided to subsequent stages of the machine learning model 502, until a final ($m^{th}$) stage of the machine learning model outputs $m^{th}$ glucose trace 810, which includes information describing both the glucose measurements 118 and the glucose measurement prediction 416.

Although depicted as including five stages, a machine learning model 412 implemented by the prediction manager 408 may include any m number of stages, where m represents an integer greater than or equal to three. Further, different ones of the various machine learning models 412 implemented by the prediction manager 408 may include different numbers of stages in comparison to one another. Each stage of the machine learning model 502(1)-502(5) is configured to generate its respective output prediction (e.g., one of glucose traces 802, 804, . . . 810) based on the model 502's training and on recognized patterns in the corresponding input provided to the model stage (e.g., glucose measurements 118 or one of the glucose traces 802, 804, . . . 808).

Because the machine learning model 502 is implemented by the prediction manager 408 in a stacked configuration with at least one other machine learning model, input to one or more of the stages of the machine learning model 502 may be supplemented with additional data 404, represented by the gray shaded arrows depicting input to each stage of the machine learning model 502(1)-502(5). In this manner, the additional data 404 may be representative of an output prediction generated by another machine learning model in the stacked configuration, such as one or more of the event predictions 414(1) or 414(2), as generated by the exercise prediction model 504 and the insulin administration 506, respectively. In turn, the respective event predictions 414(1) and 414(2) based on predictions generated by one or more of the stages of machine learning model 502.

For instance, consider an example scenario where the second glucose trace 804 is provided as input to the exercise prediction model 504 in order to make a determination as to whether an exercise event is likely to occur during the time step for which the glucose measurement prediction 416 is generated. In this scenario, based on training and patterns identified in the second glucose trace 804, the exercise prediction model 504 may generate event prediction 414(1), indicating that an exercise event is likely to occur in a future time step, such as during a future time spanning glucose traces 806, 808, and 810. In such a scenario, the exercise prediction model 504 may identify from the second glucose trace 804, that the person 102 is likely to experience an exercise response 510 (e.g., a change in glucose levels due to the exercise event) with a high degree of confidence 512. This exercise response 510 may then be provided as input to subsequent stages of the machine learning model 502 (e.g., 502(3)-(5)), such that subsequent outputs used in generating the glucose measurement prediction 416 are influenced by historical information describing the person 102's glucose level response to exercising.

Thus, the feedback loops 518 depicted in FIG. 5 are representative of the ability of the prediction manager 408 to provide intermediate outputs of different ones of the machine learning models 412 as inputs to other ones of the machine learning models 412 arranged in the stacked configuration to increase an accuracy associated with overall event predictions 414 and glucose measurement predictions 416, relative to conventional systems that do not leverage stacked model configurations or provide only historical glucose measurements as model input. The feedback loops 518 of FIG. 5 are further representative of additional data 404 that may be selectively provided as input to one or more machine learning model stages 502(1)-(5), such that additional data 404 is not necessarily provided as input via each of the shaded gray arrows.

As described herein, the additional data 404 is further representative of information obtained from sources other than outputs of various stacked machine learning models 412 implemented by the prediction manager 408. In this manner, the additional data 404 may represent any data indicative of a person's future glucose levels, such as insulin administration, carbohydrate consumption, exercise, stress, accelerometer data of a mobile device or smart watch (e.g., indicating that that the person has viewed a user interface of the device and thus has likely seen an alert or information related to glucose measurements), application data (e.g., clickstream data describing user interfaces displayed and user interactions with applications via the user interfaces), environmental temperature, barometric pressure, and the presence or absence of various health conditions (e.g., pregnancy, sickness, etc.), and so forth.

Figure 9:
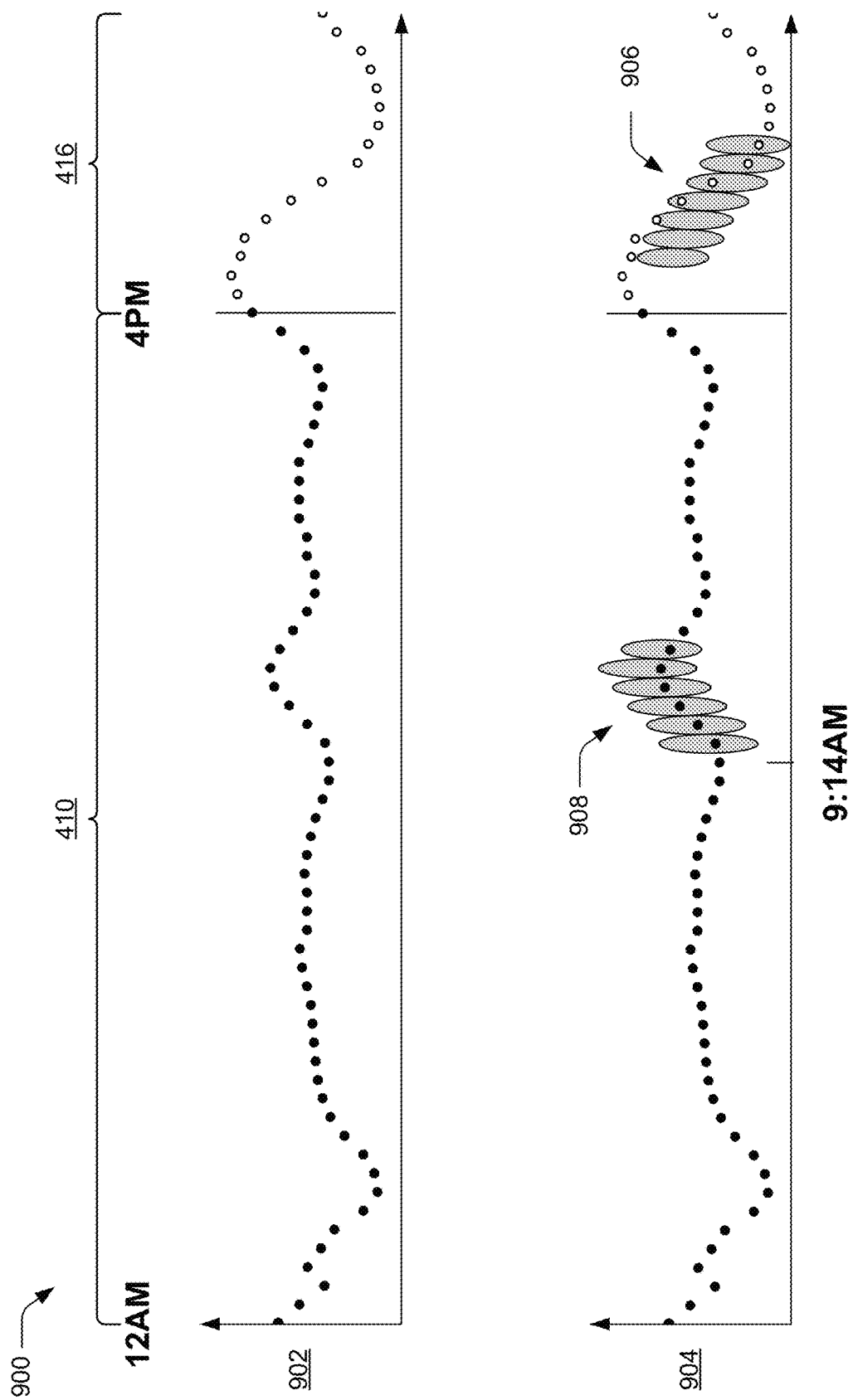
FIG. 9 depicts an additional example implementation of the prediction system of FIG. 3 in greater detail to generate an event prediction using glucose measurements, glucose measurement predictions, and information influencing the glucose measurement predictions in accordance with one or more implementations.

Having considered an example implementation of how a machine learning model 412 implemented by the prediction manager 408 is configured to output a glucose measurement prediction 416 from one or more inputs including glucose measurements 118 and additional data 404, consider the following description of how another machine learning model 412 is configured to output an event prediction 414, with respect to FIG. 9.

FIG. 9 depicts an example implementation 900 of the prediction system 310 in greater detail to generate an event prediction 414 using time sequenced glucose measurements 410, glucose measurement predictions 416, and additional data 404.

In the illustrated example 900, data 902 includes information describing example time sequenced glucose measurements 410, which may be representative of glucose measurements 118 observed for person 102 from a 12 AM starting timestamp 402 to a 4 PM ending timestamp 402. Data 902 further includes glucose measurement predictions 416, which are representative of predicted glucose levels for the person 102 occurring after 4 PM, as output by the glucose prediction model 502. By virtue of the stacked machine learning model configuration, the data 902 may be representative of additional data 404 provided as input via a feedback loop 518 to one or more of the machine learning models 412 configured to generate an event prediction 414, such as exercise prediction model 504 or insulin administration prediction model 506, as illustrated in FIG. 5.

Data 904 represents an instance of data 902 that includes event profiles 906 and 908, which may each be representative of historical patterns of glucose levels for a given user, or community of users, that are indicative of an anticipated response in glucose levels to the occurrence of an event. For instance, event profile 906 may be representative of an anticipated glucose level response to an exercise event, where each ellipses represents a range of glucose levels that define a pattern corresponding to the exercise event. In this manner, when provided the glucose measurement prediction 416 as input, the exercise prediction model 504 may be trained to recognize that a pattern of the glucose levels as indicated in the glucose measurement prediction 416 corresponds to an anticipated response 510 for an exercise event prediction 414(1). The confidence 512 associated with such an exercise event prediction 414(1) may be based at least in part on values indicated by various dots of the glucose measurements prediction 416, relative to values encompassed by the ellipses of the exercise event profile 906.

In some implementations, the confidence 512 for the exercise event prediction 414(1) may be influenced based on additional data 404 that provides additional context for the glucose measurement prediction 416. For instance, event profile 908 may correspond to a meal event that influenced values of the time sequenced glucose measurements 410 preceding the glucose measurement prediction 416. In such a scenario, a confidence value indicating whether the meal event actually occurred and influenced the corresponding glucose values encompassed by the ellipses of event profile 908 may be determined based on a variety of factors. For instance, the confidence value may be influenced by explicit user feedback confirming that a meal event commenced at 9:15 AM, may be influenced by historical data indicating that the particular user for which the glucose measurement prediction 416 is generated generally eats breakfast at 9:15 AM, combinations thereof, and so forth. In some implementations, one or more of the machine learning models 412 (1)-($n$) implemented by the prediction manager 408 may be configured to analyze historical information (e.g., historical glucose measurements 118) and generate a prediction as to whether one or more glucose level-influencing events occurred over a period encompassed by the historical information, together with a confidence value for the prediction. In this manner, in addition to leveraging explicit user feedback, the prediction manager 408 is configured to analyze and label historical user data to improve a predictive accuracy associated with a prediction 312 output by the prediction system 310.

Based on the associated confidence value, information pertaining to the occurrence of the meal event described by event profile 908 may be provided in the form of additional data 404 as input to the exercise prediction model 504 in generating the exercise event prediction output 414(1). By virtue of training the exercise prediction model 504, described in further detail below with respect to FIG. 12, the exercise prediction model 504 may utilize this prior event information to influence the level of confidence 512 associated with the exercise event prediction 414(1). For instance, the exercise prediction model 504 may be trained to identify correlations between various event responses to identify that a time separation between events corresponding to event profiles 906 and 908 correlates with historical time separations between a breakfast meal event and an afternoon workout event for a particular user.

In this manner, the event profile 908 may correspond to an event prediction 414 having a high associated confidence as output by one of the machine learning models 412. The event prediction 414 may thus be provided as input to the exercise prediction model 504 in the form of additional data 404 to generate an exercise event prediction 414(1) as corresponding to values of the glucose measurement prediction 416 aligning with event profile 906. In order to avoid negatively impacting the output of other machine learning models 412 in a stacked configuration, a determination as to whether a particular machine learning model 412's output should be included in additional data 404 provided to other machine learning models in the stack is performed based on a confidence associated with the prediction, as described in further detail below with respect to FIG. 10.

Figure 10:
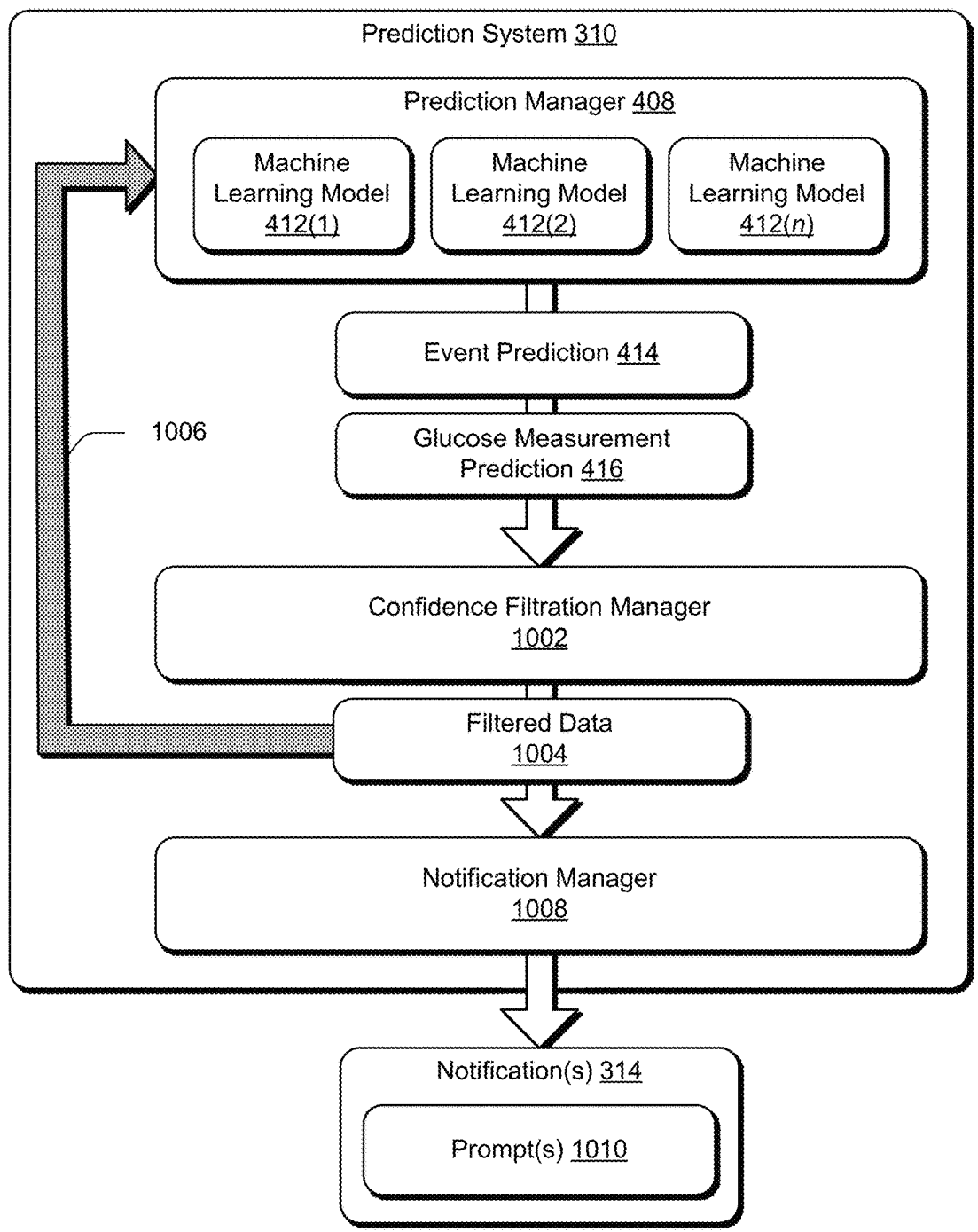
FIG. 10 depicts example implementations of the prediction system of FIG. 3 in greater detail to generate and output notifications based on event predictions and glucose measurement predictions in accordance with one or more implementations.

FIG. 10 depicts an example implementation 1000 of the prediction system 310 as filtering event predictions 414 and glucose measurement predictions 416 and generating notifications 314 for the filtered event predictions 414 and glucose measurement predictions 416 in accordance with one or more implementations.

In the illustrated example 1000, the prediction system 310 includes a confidence filtration manager 1002, which is configured to receive event predictions 414 and glucose measurement predictions 416 output by the stacked configuration of machine learning models 412(1)-(*n*), as implemented by the prediction manager 408. The filtration manager 1002 is representative of functionality of the prediction system 310 to generate filtered data 1004, which is representative of all or a subset (e.g., a proper subset) of information included in the event prediction(s) 414 and glucose measurement prediction(s) 416 output by the prediction manager 408. For instance, the filtered data 1004 may be representative of a future glucose measurement prediction 416 for a particular user over a specified time step, as well as anticipated responses 510 and 514 for the particular user due to an exercise event and an insulin administration event, respectively, occurring during the future time step.

A determination as to whether information describing the particular user's anticipated responses 510 and 514 to the respective exercise and insulin administration events in the filtered data 1004 may be performed based on the respective confidence levels 512 and 516 associated with the exercise and insulin administration events. For instance, the response 510 may be included in the filtered data 1004 only if the confidence 512 satisfies a confidence threshold (e.g., a threshold value indicating that the exercise event prediction 414(1) is likely to happen). Likewise, the response 514 may be excluded from the filtered data 1004 in response to determining that the confidence 516 fails to satisfy a confidence threshold (e.g., a threshold value indicating that the insulin administration event prediction 414(2) is likely to happen).

Information included in the filtered data 1004 may be selectively provided as input to one or more of the stacked machine learning models 412(1)-(*n*), as indicated by the arrow 1006, which is shaded to indicate that the filtered data 1004 may be representative of additional data 404 provided to one or more stages of a machine learning model 412, similar to the shaded arrows representing model input, as depicted in FIG. 5. In some implementations, the filtered data 1004 may further be leveraged by the prediction system 1010 to generate one or more of the notifications 314. Functionality of the prediction system 310 to generate notifications 314 is represented by the inclusion of notification manager 1008.

The notification manager 1008 is configured to generate and deliver notifications 314 based on the various event prediction(s) 414 and glucose measurement prediction(s) 416 output by the prediction manager 408. In some implementations, the notification 314 may include one or more prompts 1010 requesting feedback from a particular user regarding the event prediction(s) 414 and glucose measurement prediction(s) 416. For example, the notification 314 may indicate that the user is predicted to experience an insulin administration event during an upcoming time step and the prompt 1010 may request that the user confirm whether or not the insulin administration event will occur during the upcoming time step. In a similar manner, the notification 314 may indicate that the user is identified as currently exercising based on information included in the glucose measurements and the prompt 1010 may request that the user confirm whether they are currently involved in an exercise event, as well as request that the user provide further details about the exercise event.

In addition to one or more prompts 1010, the notification may include other information pertaining to one or more event predictions 414 or one or more glucose measurement predictions 416. For instance, the notification 314 may include a recommendation to take mitigating action when the notification 314 pertains to a warning that the glucose measurement prediction 416 includes dangerous glucose levels. Alternatively or additionally, the notification 314 may include information describing a confidence score associated with the prediction, such as the confidence score represented by confidences 508, 512, and 516, as illustrated in FIG. 5.

In one or more implementations, the notification 314 generated by the notification manager 1008 may be based, at least in part, on the confidence score pertaining to the event prediction 414 and/or glucose measurement prediction 416 to which the notification 314 pertains. The notification manager 1008, for example, may provide different prompts 1010, alerts, recommendations, or other messaging based in part on the confidence level associated with the prediction.

Figure 11:
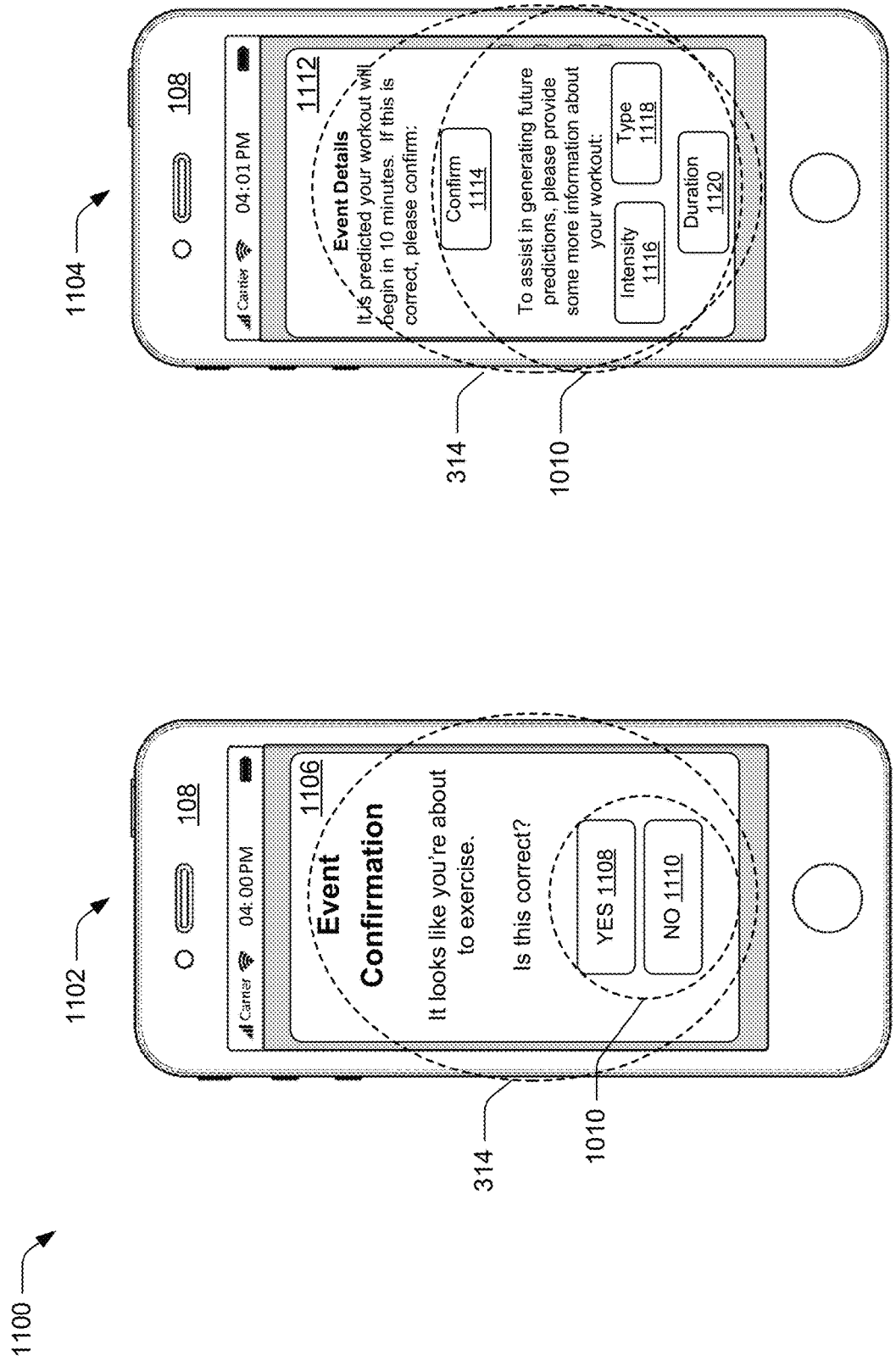
FIG. 11 depicts example implementations of user interfaces for notifying a user based on event predictions and glucose measurement predictions and receiving feedback from the notifications in accordance with one or more implementations.

In the context of outputting notifications 314 to the user, consider FIG. 11, which depicts example implementations 1100 of user interfaces displayed for notifying a user based on one or more of event prediction(s) 414 or glucose measurement prediction(s) 416.

In the illustrated example of FIG. 11, computing device 108 is depicted in various scenarios 1102 and 1104 of outputting a notification 314 including one or more prompts 1010 requesting user feedback relative to one or more of an event prediction 414 and/or a glucose measurement prediction 416. The prediction system 310 is configured to generate and output notifications 314 to the user automatically, or in response to a user request. This decision may be user-configurable, as some users may prefer to receive these predictions automatically (e.g., as they are generated by the prediction system 310), while other users may prefer to only receive these predictions only when requested.

In scenario 1102, the computing device 108 displays a user interface 1106. The user interface 1106 may correspond to an interface of an application (e.g., an interface of the CGM platform 112). Alternatively or additionally, the user interface 1106 may correspond to a "notification center" implemented by the computing device 108, such as a lock screen or other operating-level display. In scenario 1102, the user interface 1106 includes notification 314, which conveys that a machine learning model 412 implemented by the prediction system 310 determines that the user of the computing device 108 is about to experience an exercise event (e.g., is about to begin a workout). In the user interface 1106 of scenario 1102, the notification 314 includes prompts 1010 requesting user feedback regarding the event prediction 414 to which the notification 314 pertains.

Specifically, in scenario 1102, prompts 1010 include a selectable option 1108 to confirm that the event prediction 414 is correct and a selectable option 1110 to indicate that the event prediction 414 identified by the notification 314 is incorrect. The prediction system 310 may further configure the user interface 1106 such that feedback received at the prompts 1010 is automatically communicated back to the prediction system 310 for use in generating further event predictions 414 and/or glucose measurement predictions 416 (e.g., prompt 1010 feedback is communicated to the prediction system 310 in the form of additional data 404).

In some implementations, in response to receiving feedback at one or more prompts 1010 of the notification 314, the notification manager 1008 is configured to generate and transmit another notification 314 that includes prompts 1010 requesting additional information regarding the event prediction 414 and/or glucose measurement prediction 416 to which the original notification 314 pertains. For instance, in response to receiving input at selectable option 1108, the notification manager 1008 may cause output of the notification 314 depicted on the user interface 1112 of scenario 1104. Similar to user interface 1106, user interface 1112 may correspond to an interface of an application (e.g., an interface of the CGM platform 112). Alternatively or additionally, the user interface 1112 may correspond to a "notification center" implemented by the computing device 108, such as a lock screen or other operating-level display.

In scenario 1104, the user interface 1112 includes notification 314, which requests that the user provide further details regarding the prediction identified by the notification 314 of scenario 1102 (e.g., additional information about an exercise event prediction). Specifically, the notification 314 of scenario 1104 includes prompts 1010 in the form of selectable icons 1114, 1116, 1118, and 1120. Each prompt 1010 may thus be useable to specify further information about the corresponding exercise event prediction 414. For instance, input to icon 1114 may specify whether a predicted start time of the exercise event prediction 414 is accurate. Input to icon 1116 may specify a level of intensity associated with the exercise event 414, input to icon 1118 may specify a type of the exercise event 414, and input to icon 1120 may specify an anticipated duration of the exercise event 414. In this manner, the notification 314 output by prediction system 310 may include prompts 1010 requesting feedback for any type of information that describes the event prediction 414 and/or glucose measurement prediction 416 to which the notification pertains. Although described and illustrated as pertaining to the example context in which notification 314 pertains to a future event prediction 414, a notification 314 generated by the notification manager 1008 may similarly correspond to a current event prediction 414 (e.g., "Based on your glycemic response in the last 30 minutes, it looks like you're currently exercising. Is this correct?") or a past event prediction 414 (e.g., "Based on your data, it looks like you ate breakfast between 7 AM and 8 AM. Is this correct?").

User-provided feedback to prompts 1010 may be leveraged by the prediction system 310 in a variety of manners. For instance, feedback received from one or more prompts 1010 in the form of additional data 404 may be provided as input to one or more of the stacked machine learning models 412 implemented by the prediction manager 408. Alternatively or additionally, prompt 1010 feedback may be useable to adjust a confidence value associated with the prediction to which the notification 314 pertains. For instance, in an example implementation where the notification of scenario 1102 corresponds to the event prediction 414(1) generated by exercise prediction model 504, feedback to prompt 1010 confirming the accuracy of the event prediction 414(1) may cause the associated confidence 512 to be adjusted to a high value (e.g., a 100% confidence value). Alternatively or additionally, prompt 1010 feedback may be used by the prediction system 310 to train and/or generate one or more machine learning models 412 implemented by the prediction manager 408.

Although notifications 314 are illustrated and described as being communicated to a particular user, in one or more implementations at least one notification 314 may alternatively or additionally be communicated to other entities, such as a health care provider of the person 102 (e.g., a doctor), a caregiver of the person 102 (e.g., a parent or a child), and so forth. Further, a variety of other services may additionally or alternatively be provided with one or more of the notifications 314 without departing from the spirit or scope of the described techniques.

Figure 12:
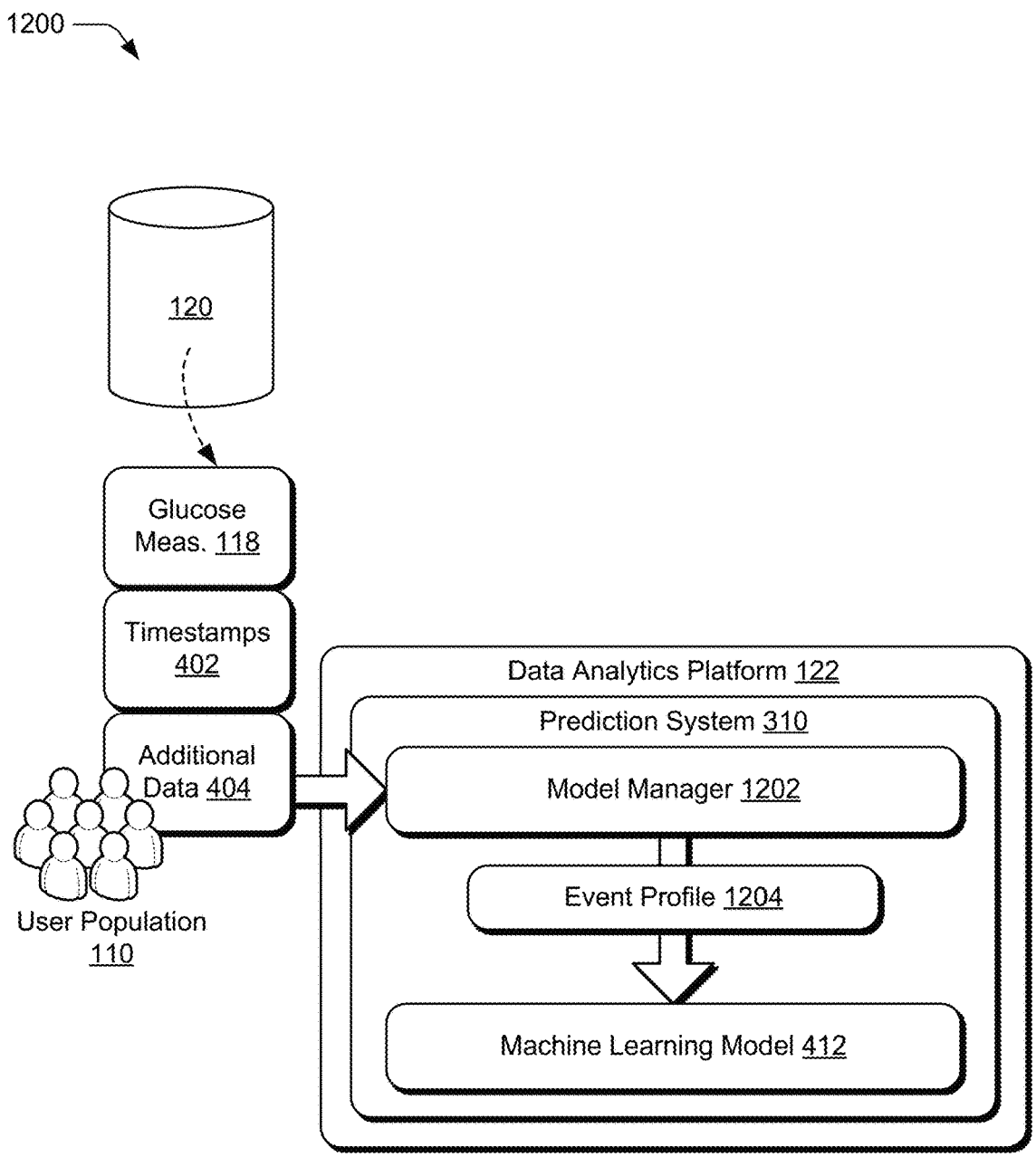
FIG. 12 depicts an example implementation of the prediction system of FIG. 3 in greater detail in which a machine learning model is trained to generate event predictions or glucose measurement predictions.

FIG. 12 depicts an example implementation 1200 of the prediction system 310 in greater detail in which a machine learning model is trained to generate an event prediction 414 or a glucose measurement prediction 416, when provided with glucose measurements 118 and/or additional data 404 as inputs. As illustrated in FIG. 3, the prediction system 310 is included as part of the data analytics platform 122, although in other scenarios the prediction system 310 may additionally or alternatively be, partially or entirely, included in other devices, such as the computing device 108.

In the illustrated example 1200, the prediction system 310 includes model manager 1202, which manages the stack of machine learning models implemented by the prediction manager 408, such as a plurality of machine learning models 412. As described above, each machine learning model 412 may be configured as a recurrent neural network, a convolutional neural network, and the like. Alternatively, the machine learning model 412 may be configured as, or include types of, other machine learning models without departing from the spirit or scope of the described techniques. These different machine learning models may be built or trained (or the model otherwise learned), respectively, using different algorithms due, at least in part, to different architectures. Accordingly, the model manager 1202's functionality is applicable to a variety of different machine learning model types and configurations. For explanatory purposes, however, functionality of the model manager 1202 will be described generally in relation to training a neural network.

Generally, the model manager 1202 is configured to manage the stacked machine learning models implemented by prediction manager 408, including the machine learning model 412. This model management includes, for example, building the machine learning model 412, training the machine learning model 412, updating this model, and so on. In one or more implementations, updating the machine learning model 412 may include transfer learning to personalize the machine learning model 412—to personalize it from a state as trained with training data of the user population 110 to an updated state trained with additional training data or (update data) describing one or more aspects of the person 102 and/or describing one or more aspects of a subset of the user population 110 determined similar to the person. Specifically, the model manager 1202 is configured to carry out model management using, at least in part, the wealth of data maintained in the storage device 120 of the CGM platform 112. As illustrated, this data includes the glucose measurements 118, timestamps 402, and additional data 404 of the user population 110. Stated differently, the model manager 1202 builds the machine learning model 412, trains the machine learning model 412 (or otherwise learns an underlying model), and updates this model using the glucose measurements 118, the timestamps 402, and the additional data 404 of the user population 110.

Unlike conventional systems, the CGM platform 112 stores (e.g., in the storage device 120) or otherwise has access to glucose measurements 118 obtained using the CGM system 104 for hundreds of thousands of users of the user population 110 (e.g., 500,000 or more). Moreover, these measurements are taken by sensors of the CGM system 104 at a continuous rate. As a result, the glucose measurements 118 available to the model manager 1202, for model building and training, number in the millions, or even billions. With such a robust amount of data, the model manager 1202 can build and train the machine learning model 412 to accurately predict whether a hypoglycemic event will occur for a person during an upcoming night time interval based on patterns in their observed glucose measurements.

Absent the robustness of the CGM platform 112's glucose measurements 118, conventional systems simply cannot build or train models to cover state spaces in a manner that suitably represents how patterns indicate future glucose levels. Failure to suitably cover these state spaces can result in hypoglycemic event predictions that are inaccurate, which can lead to results ranging from user annoyance (e.g., providing notifications indicated that a predicted hypoglycemic event will occur that does not in fact take place) to life or death situations (e.g., unsafe conditions resulting from the occurrence of hypoglycemic events during the night when none are predicted). Given the gravity of generating inaccurate and untimely predictions, it is important to build the machine learning model 412 using an amount of glucose measurements 118 that is robust against rare events.

In one or more implementations, the model manager 1202 builds the machine learning model 412 by generating training data. Initially, generating the training data includes forming training glucose measurements from the glucose measurements 118 and the corresponding timestamps 402 of the user population 110. The model manager 1202 may leverage the functionality of the sequencing manager 406 to form those training glucose measurements, for instance, in a similar manner as described in detail above in relation to forming the time sequenced glucose measurements 410. The model manager 1202 may be further implemented to generate the training glucose measurements for a specific time interval.

In one or more implementations, the model manager 1202 generates the training data to include an event profile 1204, which describes historical glucose measurements and patterns for the person 102, or groupings of users of the user population 110, that occur in relation to a corresponding event (e.g., an exercise event, an insulin administration event, a sleep or rest event, a stress event, a meal event, combinations thereof, and so forth). The event profile 1204 is representative of one or more event profiles, such as event profiles 906 and 908, as illustrated in FIG. 9, and is useable by one or more machine learning models 412 of the prediction system to more accurately determine an anticipated response (e.g., change in glucose levels) for an upcoming event.

For example, instances of training data may include labeled sections of glucose measurements, with the label identifying a type of event corresponding to the glucose measurements, synchronized with timestamps 402 to represent when the event begins and when the event ends with respect to the glucose measurements. The event labels of such training data, therefore, serve as a ground truth for comparison to the model's output during training In this manner, feedback to one or more notification prompts 1010 may further be used as ground truth training data to refine the event profile 1204 associated with a certain type of event. For instance, feedback to one or more of the prompts 1010 illustrated in FIG. 11 may be used to refine event profiles 1204 for various types of exercise events, that may be specific to the person 102 (e.g., determined based on explicit feedback provided by the person 102).

In one or more implementations, the model manager 1202 trains the machine learning model 412 to generate an event prediction 414 corresponding to the event profile 1204 using such labeled training data. In this case, the machine learning model 412 learns to generate an event prediction 414 based on inputs of one or more of glucose measurements 410 or additional data 404. In a similar manner, the machine learning model learns to generate a glucose measurement prediction 416 based on inputs of glucose measurements 410 and/or additional data 404, where the additional data 404 is representative of output predictions generated by one or more of the stacked machine learning models 412.

This process of inputting instances of the training data into the machine learning model 412, receiving training predictions from the machine learning model 412, comparing the training predictions to the ground truth information (observed) that corresponds to the generated prediction 312, and adjusting internal weights of the machine learning model 412 based on these comparisons, can be repeated for hundreds, thousands, or even millions of iterations—using an instance of training data per iteration.

The model manager 1202 may perform such iterations until the machine learning model 412 is able to generate predictions that consistently and substantially match the expected output portions. The capability of a machine learning model to consistently generate predictions that substantially match expected output portions may be referred to as "convergence." Given this, it may be said that the model manger 1202 trains the machine learning model 412 until it "converges" on a solution (e.g., the internal weights of the model have been suitably adjusted due to training iterations so that the model consistently generates predictions that substantially match the corresponding ground truth data).

As also noted above, management of the machine learning model 412 may include personalizing the machine learning model 412 using transfer learning. In such scenarios, the model manager 1202 may initially train the machine learning model 412 at the global level, as described in detail above using instances of training data generated from the data of the user population 110. In transfer learning scenarios, the model manager 1202 may then create an instance of this globally trained model for a particular user, such that a copy of the globally trained model is generated for the person 102 and other copies of the globally trained model are generated for other users on a per-user basis.

This globally trained model may then be updated (or further trained) using data specific to the person 102. For example, the model manager 1202 may create instances of training data using the glucose measurements 118 of the person 102, and further train the globally trained version of model in a similar manner as described herein (e.g., by providing training input portions of the person 102's training data to the machine learning model 412, receiving training predictions 312, comparing those predictions to respective ground truth training data, and adjusting internal weights of the machine learning model 412). Based on this further training, the machine learning model 412 is trained at a personal level, creating a personally trained machine learning model 412.

Such personalizing may be less granular than on a per-user basis, in one or more implementations. For example, the globally trained model may be personalized at a user segment level, i.e., a set of similar users of the user population 110 that is less than an entirety of the user population 110. In this way, the model manager 1202 may create copies of the globally trained machine learning model 412 on a per-segment basis and train the global versions at the segment level, creating segment specific machine learning models 412.

In one or more implementations, the model manager 1202 may personalize the machine learning model 412 at the server level (e.g., at servers of the CGM platform 112). The machine learning model 412 may then be maintained at the server level and/or communicated to the computing device 108 i.e., for integration with an application of the CGM platform 112 at the computing device 108. Alternatively or additionally, at least a portion of the model manager 1202 may be implemented at the computing device 108, such that the globally trained version of the machine learning model 412 is communicated to the computing device 108 and the transfer learning (i.e., the further training described above to personalize the model) is carried out at the computing device 108. Although transfer learning may be leveraged in one or more scenarios, such personalization may not be utilized and the described techniques may be implemented using globally trained versions of the machine learning model 412.

Having described example details of the techniques for generating event predictions and glucose measurement predictions using stacked machine learning models, consider now some example procedures to illustrate additional aspects of the techniques.

Example Procedures

This section describes example procedures for glucose measurement prediction and event prediction using stacked machine learning models. Aspects of the procedures may be implemented in hardware, firmware, or software, or a combination thereof. The procedures are shown as a set of blocks that specify operations performed by one or more devices and are not necessarily limited to the orders shown for performing the operations by the respective blocks. In at least some implementations the procedures are performed by a prediction system, such as prediction system 310 that makes use of the sequencing manager 406, the prediction manager 408, the notification manager 1008, and the model manager 1202.

Figure 13:
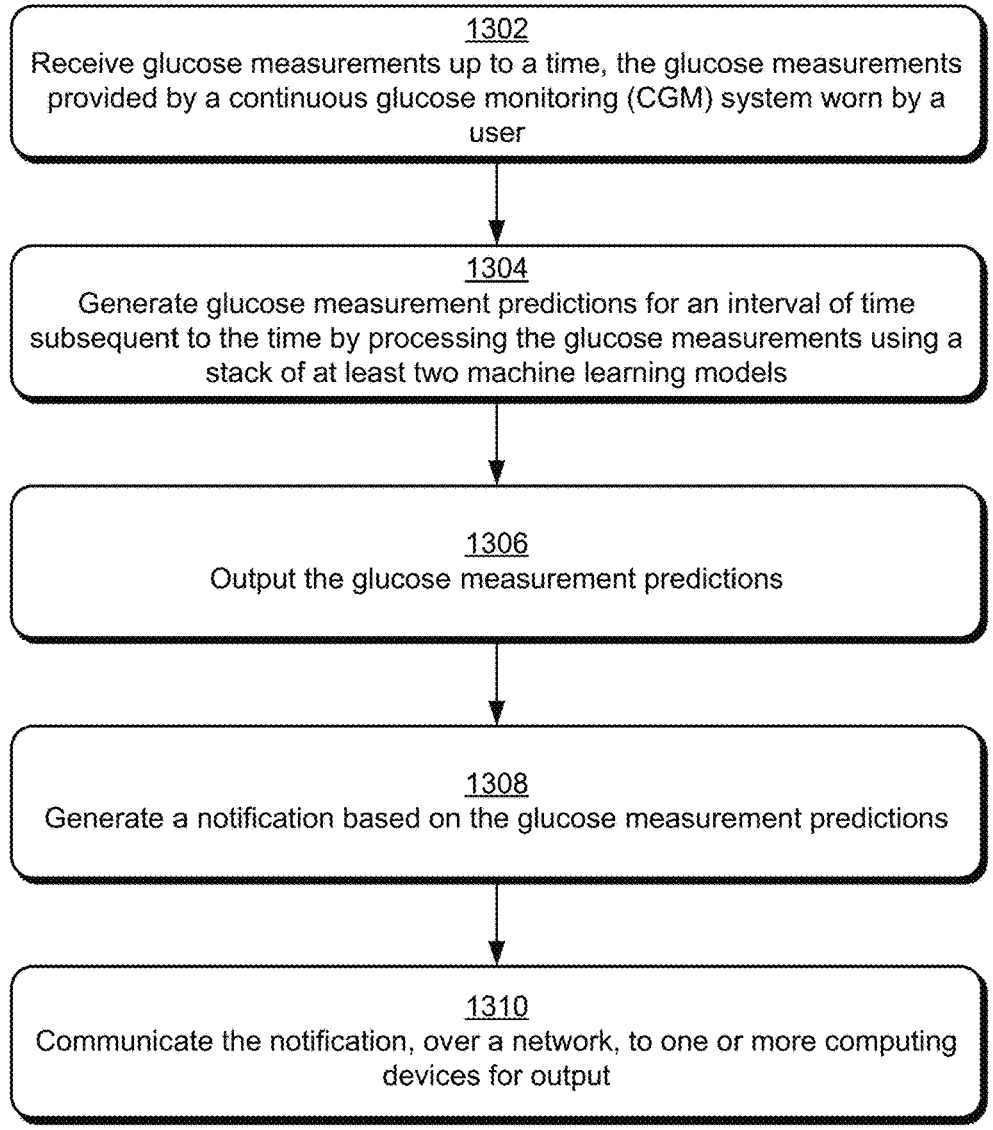
FIG. 13 depicts a procedure in an example implementation in which a stack of machine learning models generates event predictions and glucose measurement predictions based on historical glucose measurements.

FIG. 13 depicts a procedure 1300 in an example implementation in which a stack of machine learning models generates a glucose measurement prediction based on glucose measurements and additional data.

Glucose measurements up to a time are received (block 1302). In accordance with the principles described herein, the glucose measurements are provided by a continuous glucose monitoring (CGM) system worn by a user. By way of example, prediction manager 408 receives the glucose measurements 118, where the glucose measurements are obtained from the CGM system 104 worn by the person 102. In particular, the CGM system 104 includes the sensor 202, which is inserted subcutaneously into skin of the person 102 and used to measure glucose in the person 102's blood.

The glucose measurements are processed using a stack of at least two machine learning models to generate glucose measurement predictions for an interval of time subsequent to the time (block 1304). In accordance with the principles described herein, individual models of the stack of multiple machine learning models are generated based on historical of glucose measurements of a user population and or additional data describing one or more behaviors of the user population. By way of example, the stack of multiple machine learning models 412(1)-(n) processes the glucose measurements 118 to generate glucose measurement prediction 416. The stack of multiple machine learning models 412(1)-(n) generates glucose measurement prediction by processing glucose measurements 118 and/or additional data 404 based on patterns, learned during training, relative to the person 102 or a user population 110 for which the glucose measurement prediction 416 is generated. As noted above, the user population 110 includes users that wear CGM systems, such as the CGM system 104.

The glucose measurement predictions are then output (block 1306). By way of example, the prediction system 310 outputs the glucose measurement prediction 416, such as for processing by additional logic (e.g., to generate recommendations or notifications), for storing in the storage device 120, for communication to one or more computing devices, or for display, to name just a few.

A notification is generated based on the glucose measurement predictions (block 1308). By way of example, the data analytics platform 122 generates the notification 314 based on the glucose measurement prediction 416. For instance, the notification 314 may alert a user (or a health care provider or telemedicine service) about an upcoming adverse health condition, such as that the user is likely to administer an incorrect dose of insulin for their predicted glucose levels absent a mitigating behavior (e.g., eating, exercising, and so forth). Additionally or alternatively, the notification 314 may provide support for deciding how to treat diabetes, such as by recommending a user (or a health care provider or telemedicine service) perform an action (e.g., download an app to the computing device 108, seek medical attention immediately, dose insulin, go for a walk, consume a particular food or drink), continue a behavior (e.g., continue eating a certain way or exercising a certain way), change a behavior (e.g., change eating habits or exercise habits), and so on. The notification may further include one or more prompts 1010, requesting that a user (e.g., person 102) provide feedback relative to the glucose measurement prediction 416.

The notification is communicated, over a network, to one or more computing devices for output (block 1310). By way of example, a communication interface of the data analytics platform 122 communicates the notification 314 over the network 116 to the computing device 108 of the person 102 (e.g., to computing device 108 for output via an application of the CGM platform 112). Additionally or alternatively, the data analytics platform 122 communicates the notification 314 over the network 116 to a computing device associated with a health care provider (not shown) and/or a computing device associated with a telemedicine service (not shown) (e.g., to a telemedicine service for output via a provider portal).

Figure 14:
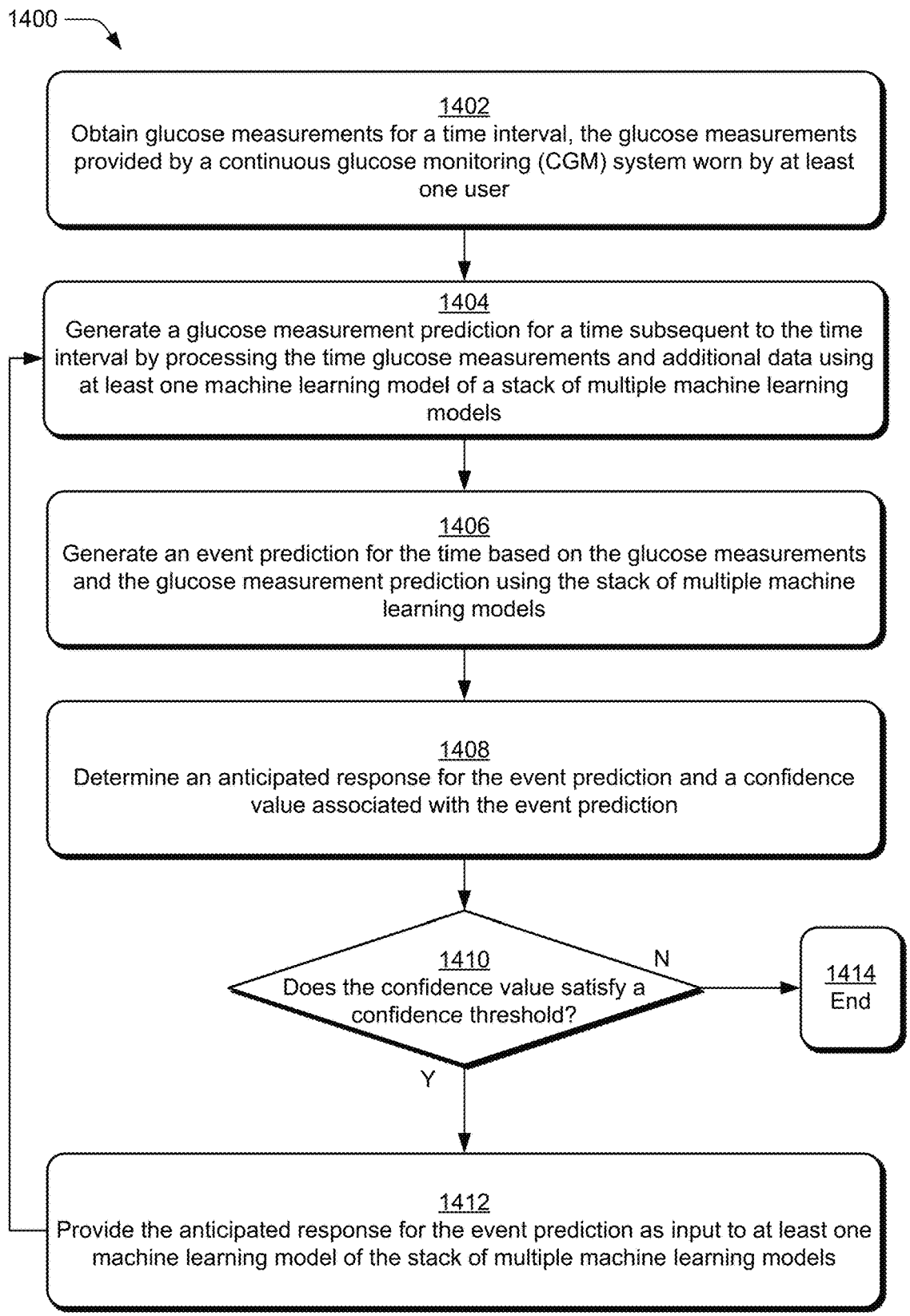
FIG. 14 depicts a procedure in an example implementation in which prediction information output by a machine learning model of a stack of machine learning model is selectively filtered as input to at least one other model of the stack of machine learning models based on a confidence level associated with the output prediction information.

FIG. 14 depicts a procedure 1400 in an example implementation in which a stack of multiple machine learning models is trained to output predictions specifying one or more of an event prediction or a glucose measurement prediction based on historical glucose measurements of a user population and additional data that includes one or more outputs from the stack of multiple machine learning models.

Glucose measurements for a time interval are received (block 1402). In accordance with the principles described herein, the glucose measurements are provided by a continuous glucose monitoring (CGM) system worn by at least one user of a user population, such as person 102 of user population 110. By way of example, the prediction manager 408 receives the glucose measurements 118 from the sequencing manager 406 of the prediction system 310, such as in the form of time sequenced glucose measurements 410.

In this manner, the time sequenced of glucose measurements 410 may correspond to an aggregation and ordering of glucose measurements 118 and timestamps 102 as obtained by the CGM system 104 worn by person 102. In particular, the CGM system 104 includes the sensor 202, which is inserted subcutaneously into skin of the person 102 and used to measure glucose in the person 102's blood.

A glucose measurement prediction for a time subsequent to the time interval is generated by processing the time sequence of glucose measurements and additional data using at least one machine learning model of a stack of machine learning models (block 1404). The prediction manager 408, for instance, provides the glucose measurements 118 and the additional data 404 as input to one of the stacked machine learning models 412(1)-(n) that is trained to generate glucose measurement prediction 416. In accordance with one or more implementations, the stacked machine learning models 412 may be trained to identify patterns in glucose measurements 118 and/or the additional data 404 to generate a prediction of glucose levels for the person 102 during the time subsequent to the time interval. In implementations, the glucose measurement prediction 416 may be output together with a confidence value 508, indicating a degree of confidence pertaining to the accuracy of the glucose measurement prediction 416 as output by the prediction manager 408.

An event prediction is then generated for the time based on the glucose measurements and the glucose measurement prediction using the stack of machine learning models (block 1406). The prediction manager 408, for instance, provides the glucose measurement prediction 416 generated by glucose prediction model 502 to one or more machine learning models of the stack of machine learning models 412(1)-(n), such as to one or more of the exercise prediction model 504 or the insulin administration prediction model 506, as illustrated in FIG. 5. The glucose measurement prediction 416 is provided as input to at least one other one of the stacked machine learning models 412 via a feedback loop 518, and is thus representative of additional data 404 that may be provided as input to the stacked machine learning models 412(1)-(n).

The prediction manager 408, for instance, provides the time sequenced glucose measurements 410 and the additional data 404 (e.g., the glucose measurement prediction 416) as inputs to one of the stacked machine learning models 412(1)-(n) that is trained to generate an event prediction 414. In accordance with one or more implementations, such a machine learning model 412 may be trained to identify patterns in the time sequenced glucose measurements 410 together with the additional data 404 to generate a prediction that a specified event (e.g., meal, insulin administration, sleep/rest, exercise, stress, and so forth) will occur during the time subsequent to the time interval. The exercise prediction model 504, for instance, may identify that an exercise event is likely to occur during the time subsequent to the time interval, based on patterns included in the time sequenced glucose measurements 410, the glucose measurement prediction 416, and/or additional data 404. In response to such an identification, the exercise prediction model 504 may output event prediction 414(1), indicating that an exercise event is likely to occur.

An anticipated response to the event identified by the event prediction and a confidence value associated with the event prediction are then determined (block 1408). The exercise prediction model 504, for instance, may be trained by the model manager 1202 to output the event prediction 414(1) together with an anticipated response 510 for the corresponding event as well as a degree of confidence 512 that the corresponding event will occur during the time subsequent to the time interval. The response 510 may be indicative of one or more glucose levels, as well as changes to glucose levels of the person 102 occurring in response to the event describe by event prediction 414(1) (e.g., an exercise event). In implementations, the degree of confidence 512 may be expressed as a numerical value between zero and one, inclusive, where zero expresses no confidence that the event will occur and one expresses a highest degree of confidence that the event will occur.

A determination is then made as to whether the confidence value satisfies a confidence threshold (block 1410). The confidence filtration manager 1002 of the prediction system 310, for instance, may compare the confidence 512 for the event prediction 414(1) to a confidence threshold specifying an acceptable degree of confidence for determining whether to provide an output of one stacked machine learning model 412 as input to the stack of machine learning models 412(1)-(n). The confidence threshold may be any suitable value (e.g., 90% confidence) and may be dependent on the particular type of machine learning model 412 that generated the corresponding event prediction, such that different ones of the stacked machine learning models 412(1)-(n) are associated with different confidence thresholds. In some implementations, the confidence threshold may be specified by a user of the computing device implementing the prediction system 310 (e.g., person 102). Alternatively or additionally, the confidence threshold may be determined by the prediction system 310 on a user-specific basis, such that different users of the user population 110 are assigned different confidence thresholds.

In response to determining that the confidence value satisfies the confidence threshold, the anticipated response for the event prediction as input to at least one machine learning model of the stack of multiple machine learning models (block 1412). The response 510, for instance, may be provided as input to one or more of the machine learning models 412, such as input to glucose prediction model to generate glucose measurement prediction 416 or insulin administration prediction model 506 to generate event prediction 414(2). Communication of the anticipated response may be performed via the feedback loop 518, which in turn is enabled by the stacked configuration of machine learning models 412(1)-(n) implemented by the prediction manager 408. Operation may then return to block 1404, such that the stack of multiple machine learning models 412(1)-(n) can continue to generate event prediction(s) 414 and glucose measurement prediction(s) 416 with the added benefit of information described by one or more predictions 312 generated by the prediction manager 408.

This cycle of operations described in blocks 1404-1412 may continue until a determination is made that a confidence value associated with an event prediction 414 and/or a glucose measurement prediction 416 fails to satisfy a corresponding confidence threshold, at which point operations cease (block 1414). Alternatively, rather than ceasing performance of operations described in blocks 1404-1412, in response to determining that one confidence value associated with an event prediction 414 or a glucose measurement prediction 416 fails to satisfy a corresponding confidence threshold, the one confidence value may be discarded and prevented from being provided as input to the stacked machine learning models 412(1)-(n). Operations described in blocks 1404-1412 may thus continue using only filtered data 1004 generated by the confidence filtration manager 1002, thereby ensuring that respective predictions 312 output by different ones of the stacked machine learning models 412(1)-(*n*) are not negatively impacted by processing input data not representative of actual conditions (e.g., future actual glucose levels of the person 102 or future actual events experienced by the person 102).

Figure 15:
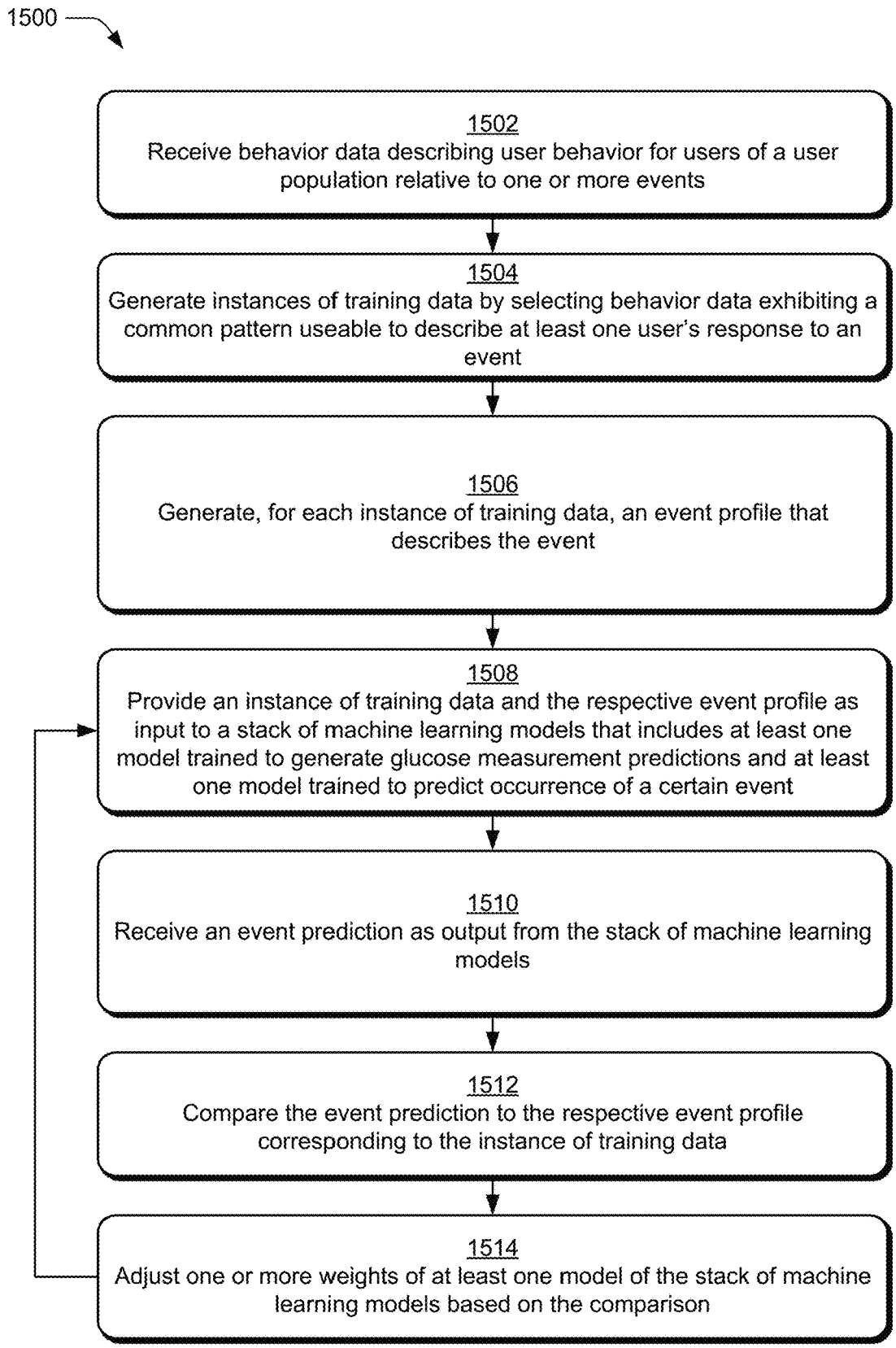
FIG. 15 depicts a procedure in an example implementation in which a stack of machine learning models is trained to generate event predictions and glucose measurement predictions based on historical glucose measurements of a user population.

FIG. 15 depicts a procedure 1500 in an example implementation in which a stack of machine learning models are trained to generate event predictions for a user population.

Behavior data describing user behavior for users of a user population relative to one or more events is received (block 1502). In accordance with the principles described herein, the behavior data may include glucose measurements provided by CGM systems worn by users of a user population 110 and/or additional data 404 received from one or more sources other than the CGM systems. By way of example, the prediction system 310 obtains the glucose measurements 118 of users of the user population 110. In some implementations, the prediction system additionally obtains the timestamps 402 of glucose measurements 118 and forms time sequenced glucose measurements 410.

The prediction system 310 additionally obtains additional data 404 from one or more sources. The additional data 404 is representative of information useable to describe various aspects that may impact glucose, and may be correlated in time with glucose measurements 118 (e.g., based on timestamps associated with the additional data 404). Such additional data 404 may include, by way of example and not limitation, application usage data (e.g., clickstream data describing user interfaces displayed and user interactions with applications via the user interfaces), accelerometer data of a mobile device or smart watch (e.g., indicating that that the person has viewed a user interface of the device and thus has likely seen an alert or information related to a predicted event), explicit feedback to notification prompts requesting input on a user's current or planned activities, data describing insulin administered (e.g., timing and insulin doses), data describing food consumed (e.g., timing of food consumption, type of food, and/or amount of carbohydrates consumed, activity data from various sensors (e.g., step data, workouts performed, or other data indicative of user activity or exercise), glucose level responses to stress, combinations thereof and so forth.

Instances of training data are generated by selecting behavior data exhibiting one or more common patterns useable to describe at least one user's response to a certain event (block 1504). In accordance with the principles described herein, the common patterns may represent changes in glucose levels that occur leading up to, during, and following a certain event (e.g., a meal, insulin administration, sleep/rest, exercise, stress, and so forth). In some implementations the common pattern(s) may be identified by correlating the changes in glucose levels with timestamps 402 used to generate the time sequenced glucose measurements 410, and further correlated with information included in additional data 404.

An event profile is generated for each instance of training data (block 1506). In accordance with the principles described herein, each event profile defines the respective instance of training data as corresponding to a certain type of event, together with an anticipated response for a particular user or group of users relative to the event (e.g., an anticipated change in glucose levels for a particular person participating in, or otherwise subject to, the certain type of event). By way of example, the model manager 1202 generates, for each instance of training data, an event profile 1204 that defines at least a start timestamp and an end timestamp for the corresponding event, relative to the one or more patterns identified in the glucose measurements 118 and/or additional data 404. For example, the model manager 1202 may generate event profile 908 for person 102 to represent the person 102's anticipated glucose response to breakfast and may generate event profile 906 for the person 102's response to an afternoon workout. The event profiles, therefore, serve as a ground truth for comparison to outputs of the stacked machine learning models 412(1)-(*n*) during training.

In the illustrated procedure 1500, blocks 1508-1514 may be repeated until the stack of multiple machine learning models is suitably trained, such as until each of the machine learning models in the stacked configuration "converges" on a solution (e.g., until the internal weights of the model have been suitably adjusted due to training iterations so that the model consistently generates predictions that substantially match the expected output portions). Additionally or alternatively, the blocks 1508-1514 may be repeated for a number of instances (e.g., all instances) of the training data.

An instance of training data and the respective event profile is provided as input to a stack of multiple machine learning models that includes at least one model trained to generate glucose measurement predictions and at least one model trained to generate event predictions (block 1508). By way of example, the model manager 1202 provides an instance of training data generated at block 1504 and the respective event profile generated at block 1506 as input to the stacked machine learning models 412(1)-(*n*).

An event prediction is received as output from the stack of machine learning models (block 1510). By way of example, machine learning model 412(*n*) generates event prediction 414(2), such as a prediction that an insulin administration event will occur in an upcoming time step.

The event prediction is compared to the respective event profile of the instance of training data (block 1512). By way of example, the model manager 1202 compares the event prediction generated at block 1510 to the respective event profile of the training instance generated at block 1506 (e.g., by using a loss function such as mean squared error (MSE)). Although described with respect to MSE, the model manager 1202 may use other loss functions during training, to compare the predictions 312 output by the stacked machine learning models 412(1)-(*n*) to a ground truth for the output, without departing from the spirit or scope of the described techniques.

Weights of one or more of the stacked machine learning models are adjusted based on the comparison (block 1514). By way of example, the model manager 1202 may adjust internal weights of at least one machine learning model 412 based on the comparing so that the machine learning model 412 can substantially reproduce the expected event profile (e.g., whether an insulin administration event will occur) when one or more of glucose measurements 118, additional data 404, event prediction(s) 414, or glucose measurement prediction(s) 416 are provided in the future as input.

Having described example procedures in accordance with one or more implementations, consider now an example system and device that can be utilized to implement the various techniques described herein.

Example System and Device

Figure 16:
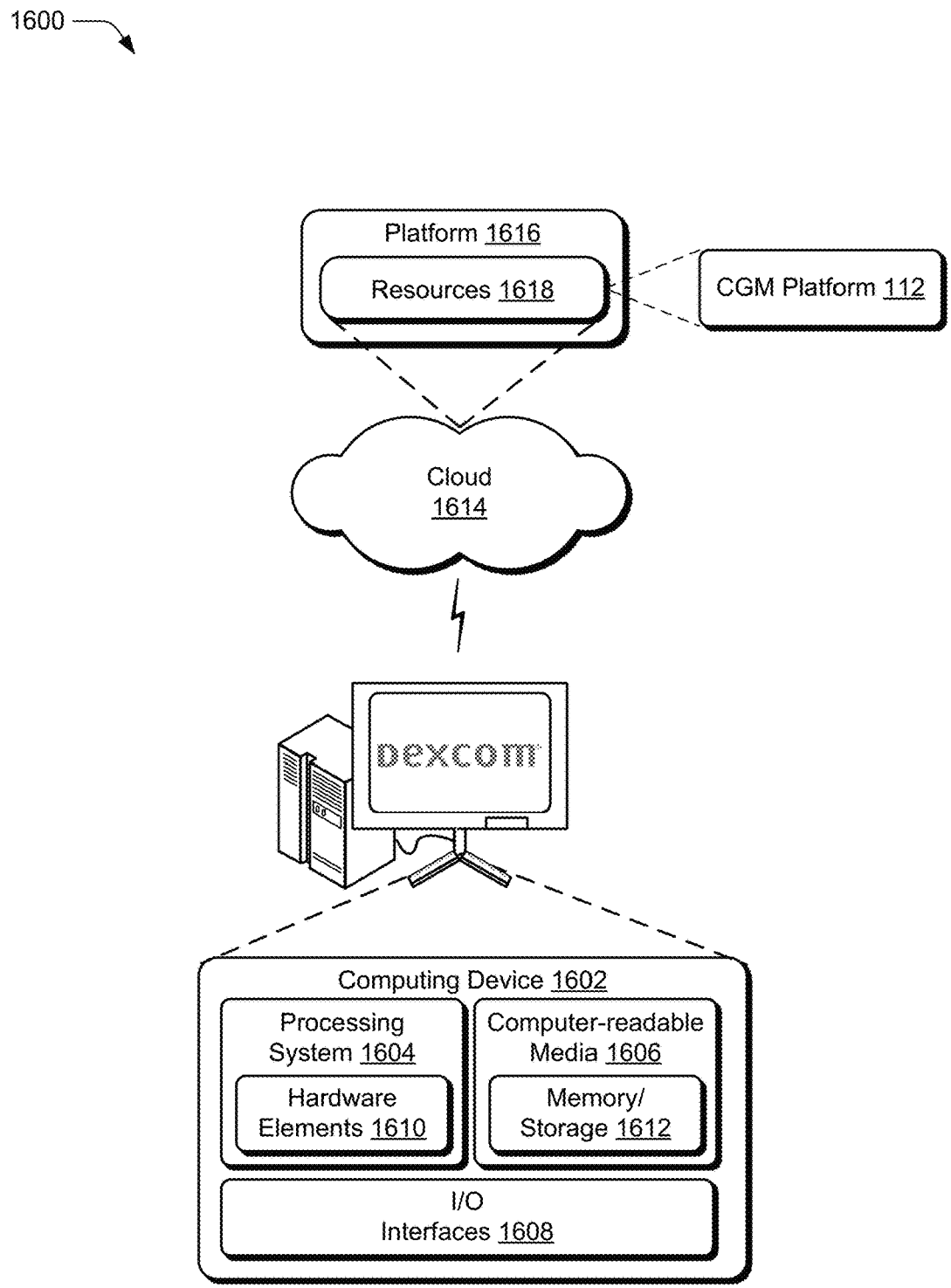
FIG. 16 illustrates an example system that includes an example computing device that is representative of one or more computing systems and/or devices that may implement the various techniques described herein.

FIG. 16 illustrates an example system generally at 1600 that includes an example computing device 1602 that is representative of one or more computing systems and/or devices that may implement the various techniques described herein. This is illustrated through inclusion of the CGM platform 112. The computing device 1602 may be, for example, a server of a service provider, a device associated with a client (e.g., a client device), an on-chip system, and/or any other suitable computing device or computing system.

The example computing device 1602 as illustrated includes a processing system 1604, one or more computer-readable media 1606, and one or more I/O interfaces 1608 that are communicatively coupled, one to another. Although not shown, the computing device 1602 may further include a system bus or other data and command transfer system that couples the various components, one to another. A system bus can include any one or combination of different bus structures, such as a memory bus or memory controller, a peripheral bus, a universal serial bus, and/or a processor or local bus that utilizes any of a variety of bus architectures. A variety of other examples are also contemplated, such as control and data lines.

The processing system 1604 is representative of functionality to perform one or more operations using hardware. Accordingly, the processing system 1604 is illustrated as including hardware elements 1610 that may be configured as processors, functional blocks, and so forth. This may include implementation in hardware as an application-specific integrated circuit or other logic device formed using one or more semiconductors. The hardware elements 1610 are not limited by the materials from which they are formed or the processing mechanisms employed therein. For example, processors may comprise semiconductor(s) and/or transistors (e.g., electronic integrated circuits (ICs)). In such a context, processor-executable instructions may be electronically-executable instructions.

The computer-readable media 1606 is illustrated as including memory/storage 1612. The memory/storage 1612 represents memory/storage capacity associated with one or more computer-readable media. The memory/storage component 1612 may include volatile media (such as random access memory (RAM)) and/or nonvolatile media (such as read only memory (ROM), Flash memory, optical disks, magnetic disks, and so forth). The memory/storage component 1612 may include fixed media (e.g., RAM, ROM, a fixed hard drive, combinations thereof, and so forth) as well as removable media (e.g., Flash memory, a removable hard drive, an optical disc, combinations thereof, and so forth). The computer-readable media 1606 may be configured in a variety of other manners, as described in further detail below.

Input/output interface(s) 1608 are representative of functionality to enable a user to enter commands and/or information to computing device 1602, and to enable information to be presented to the user and/or other components or devices using various input/output devices. Examples of input devices include a keyboard, a cursor control device (e.g., a mouse), a microphone, a scanner, touch functionality (e.g., capacitive or other sensors configured to detect physical touch), a camera (e.g., a device configured to employ visible or non-visible wavelengths such as infrared frequencies to recognize movement as gestures that do not involve touch), and so forth. Examples of output devices include a display device (e.g., a monitor or projector), speakers, a printer, a network card, tactile-response device, and so forth. Thus, the computing device 1602 may be configured in a variety of ways as further described below to support user interaction.

Various techniques may be described herein in the general context of software, hardware elements, or program modules. Generally, program modules include routines, programs, objects, elements, components, data structures, and so forth that perform particular tasks or implement particular abstract data types. The terms "module," "functionality," and "component" as used herein generally represent software, firmware, hardware, or combinations thereof. The features of the techniques described herein are platform-independent, meaning that the techniques may be implemented on a variety of commercial computing platforms having a variety of processors.

An implementation of the described modules and techniques may be stored on or transmitted across some form of computer-readable media. The computer-readable media may include a variety of media that may be accessed by the computing device 1602. By way of example, and not limitation, computer-readable media may include "computer-readable storage media" and "computer-readable signal media."

"Computer-readable storage media" may refer to media and/or devices that enable persistent and/or non-transitory storage of information, in contrast to mere signal transmission, carrier waves, or signals per se. Thus, computer-readable storage media refers to non-signal bearing media. The computer-readable storage media includes hardware such as volatile and non-volatile, removable and non-removable media and/or storage devices implemented in a method or technology suitable for storage of information such as computer readable instructions, data structures, program modules, logic elements/circuits, or other data. Examples of computer-readable storage media may include, but are not limited to, RAM, ROM, EEPROM, flash memory or other memory technology, CD-ROM, digital versatile disks (DVD) or other optical storage, hard disks, magnetic cassettes, magnetic tape, magnetic disk storage or other magnetic storage devices, or other storage device, tangible media, or article of manufacture suitable to store the desired information and which may be accessed by a computer.

"Computer-readable signal media" may refer to a signal-bearing medium that is configured to transmit instructions to the hardware of the computing device 1602, such as via a network. Signal media typically may embody computer readable instructions, data structures, program modules, or other data in a modulated data signal, such as carrier waves, data signals, or other transport mechanism. Signal media also include any information delivery media. The term "modulated data signal" means a signal that has one or more of its characteristics set or changed in such a manner as to encode information in the signal. By way of example, and not limitation, communication media include wired media such as a wired network or direct-wired connection, and wireless media such as acoustic, RF, infrared, and other wireless media.

As previously described, hardware elements 1610 and computer-readable media 1606 are representative of modules, programmable device logic and/or fixed device logic implemented in a hardware form that may be employed in some embodiments to implement at least some aspects of the techniques described herein, such as to perform one or more instructions. Hardware may include components of an integrated circuit or on-chip system, an application-specific integrated circuit (ASIC), a field-programmable gate array (FPGA), a complex programmable logic device (CPLD), and other implementations in silicon or other hardware. In this context, hardware may operate as a processing device that performs program tasks defined by instructions and/or logic embodied by the hardware as well as a hardware utilized to store instructions for execution, e.g., the computer-readable storage media described herein.

Combinations of the foregoing may also be employed to implement various techniques described herein. Accordingly, software, hardware, or executable modules may be implemented as one or more instructions and/or logic embodied on some form of computer-readable storage media and/or by one or more hardware elements 1610. The computing device 1602 may be configured to implement particular instructions and/or functions corresponding to the software and/or hardware modules. Accordingly, implementation of a module that is executable by the computing device 1602 as software may be achieved at least partially in hardware, e.g., through use of computer-readable storage media and/or hardware elements 1610 of the processing system 1604. The instructions and/or functions may be executable/operable by one or more articles of manufacture (for example, one or more computing devices 1602 and/or processing systems 1604) to implement techniques, modules, and examples described herein.

The techniques described herein may be supported by various configurations of the computing device 1602 and are not limited to the specific examples of the techniques described herein. This functionality may also be implemented all or in part through use of a distributed system, such as over a "cloud" 1614 via a platform 1616 as described below.

The cloud 1614 includes and/or is representative of a platform 1616 for resources 1618. The platform 1616 abstracts underlying functionality of hardware (e.g., servers) and software resources of the cloud 1614. The resources 1618 may include applications and/or data that can be utilized while computer processing is executed on servers that are remote from the computing device 1602. Resources 1618 can also include services provided over the Internet and/or through a subscriber network, such as a cellular or Wi-Fi network.

The platform 1616 may abstract resources and functions to connect the computing device 1602 with other computing devices. The platform 1616 may also serve to abstract scaling of resources to provide a corresponding level of scale to encountered demand for the resources 1618 that are implemented via the platform 1616. Accordingly, in an interconnected device embodiment, implementation of functionality described herein may be distributed throughout the system 1600. For example, the functionality may be implemented in part on the computing device 1602 as well as via the platform 1616 that abstracts the functionality of the cloud 1614.

Conclusion

Although the systems and techniques have been described in language specific to structural features and/or methodological acts, it is to be understood that the systems and techniques defined in the appended claims are not necessarily limited to the specific features or acts described. Rather, the specific features and acts are disclosed as example forms of implementing the claimed subject matter.

What is claimed is:

1. A method comprising:
    (a) receiving, at a first processor, data describing behavior of a user up to a time;
    (b) generating, at the first processor, a behavioral event prediction indicative of whether the user will engage in an activity during an interval of time subsequent to the time by providing the data describing behavior of the user as input to a first one of a plurality of machine learning models arranged in a stacked configuration;
    (c) receiving, at the first processor, glucose measurements for the user up to the time, the glucose measurements provided by a continuous glucose monitoring system configured to be worn by the user;
    (d) generating, at the first processor, a glucose measurement prediction, based on the behavioral event prediction, for the interval of time subsequent to the time by providing the behavioral event prediction and the glucose measurements as input to a second one of the plurality of machine learning models arranged in the stacked configuration;
    (e) outputting, by the first processor, the glucose measurement prediction;
    (f) receiving, at a second processor, a set of glucose measurements for the user;
    (g) adjusting, by the second processor, a weight of the second one of the plurality of machine learning models based on the set of glucose measurements and the glucose measurement prediction, wherein the stacked configuration of the plurality of machine learning models enables an output generated by one of the plurality of machine learning models to be provided as input to at least another one of the plurality of machine learning models to increase an accuracy associated with glucose measurement predictions; and
    repeating steps (a)-(e) to generate a second glucose measurement prediction using the second one of the plurality of machine learning models with the adjusted weight.

2. The method of claim 1, wherein providing the behavioral event prediction as input to the second one of the plurality of machine learning models comprises filtering information associated with the behavioral event prediction based on a confidence threshold associated with the first one of the plurality of machine learning models.

3. The method of claim 1, further comprising training the first one of the plurality of machine learning models by:
    receiving data describing user behavior for users of a user population; and
    generating instances of training data by:
        selecting behavior data exhibiting a common pattern useable to describe a response to an event for at least one user of the user population;
        defining an event profile for the event, the event profile specifying a type of the event and the response to the event; and
        training the first one of the plurality of machine learning models to predict occurrence of the event using the instances of training data by:
            providing the instances of training data to the first one of the plurality of machine learning models;
            receiving, for each instance of training data, an event prediction from the first one of the plurality of machine learning models indicating whether the event will occur over time encompassed by the instance of training data;
            comparing, for each instance of training data, the event prediction to the event profile; and
            adjusting at least one weight of the first one of the plurality of machine learning models based on the comparing.

4. The method of claim 1, further comprising:
    generating at least the second one of the plurality of machine learning models based on glucose measurements of a user population; and generating at least the first one of the plurality of machine learning models based on additional data of the user population.

5. The method of claim 1, further comprising:
generating a third one of the plurality of machine learning models based on glucose measurements of a user population;
generating a fourth one of the plurality of machine learning models based on additional data of the user population;
causing the third one of the plurality of machine learning models generated based on the glucose measurements of the user population to output a first initial glucose measurement prediction;
providing the first initial glucose measurement prediction as input to the fourth one of the plurality of machine learning models generated based on the additional data of the user population;
causing the fourth one of the plurality of machine learning models generated based on the additional data of the user population to output a second initial glucose measurement prediction; and
providing the second initial glucose measurement prediction as input to the first one of the plurality of machine learning models or the second one of the plurality of machine learning models.

6. The method of claim 1, further comprising:
generating a third one of the plurality of machine learning models based on glucose measurements of a user population;
generating a fourth one of the plurality of machine learning models based on additional data of the user population;
causing the fourth one of the plurality of machine learning models generated based on the additional data of the user population to generate an instance of training data;
providing the instance of training data as input to the third one of the plurality of machine learning models generated based on the glucose measurements of the user population;
causing the third one of the plurality of machine learning models generated based on the glucose measurements of the user population to output an event profile for the instance of training data; and
providing the event profile and the instance of training data as input to the first one of the plurality of machine learning models or the second one of the plurality of machine learning models.

7. The method of claim 1, further comprising generating the first one of the plurality of machine learning models by:
receiving historical glucose measurements of a user population, the historical glucose measurements provided by continuous glucose monitoring systems worn by users of the user population;
generating instances of training data by selecting, for each instance of training data, glucose measurements from the historical glucose measurements and generating an event profile defining the instance of training data as including the activity and glucose level changes relative to the activity; and
training the first one of the plurality of machine learning models to predict occurrence of the activity using the instances of training data and the corresponding event profiles.

8. The method of claim 1, wherein the second one of the plurality of machine learning models is a recurrent neural network configured to iteratively generate the glucose measurement prediction, each iteration generating measurements for a portion of the glucose measurement prediction.

9. The method of claim 8, wherein the first one of the plurality of machine learning models is a reinforcement learning model updated on feedback regarding the behavioral event prediction.

10. The method of claim 1, wherein the glucose measurements include at least one current glucose measurement.

11. A computing system, comprising:
a first computing device:
a first memory comprising executable instructions;
a first processor in data communication with the first memory and configured to execute the instructions to:
(a) receive data describing behavior of a user up to a time;
(b) generate a behavioral event prediction indicative of whether the user will engage in an activity during an interval of time subsequent to the time by providing the data describing behavior of the user as input to a first one of a plurality of machine learning models arranged in a stacked configuration;
(c) receive glucose measurements for the user up to the time, the glucose measurements provided by a continuous glucose monitoring system configured to be worn by the user;
(d) generate a glucose measurement prediction, based on the behavioral event prediction, for the interval of time subsequent to the time by providing the behavioral event prediction and the glucose measurements as input to a second one of the plurality of machine learning models arranged in the stacked configuration;
(e) output the glucose measurement prediction; and
a second computing device:
a second memory comprising executable instructions;
a second processor in data communication with the second memory and configured to execute the instructions to:
(f) receive a set of glucose measurements for the user; and
(g) adjust a weight of the second one of the plurality of machine learning models based on the set of glucose measurements and the glucose measurement prediction,
wherein the stacked configuration of the plurality of machine learning models enables an output generated by one of the plurality of machine learning models to be provided as input to at least another one of the plurality of machine learning models to increase an accuracy associated with glucose measurement predictions, and
wherein the first processor is further configured to repeat steps (a)-(e) to generate a second glucose measurement prediction using the second one of the plurality of machine learning models with the adjusted weight.

12. The computing system of claim 11, wherein the first processor is further configured to execute the instructions to:
provide the behavioral event prediction as input to the second one of the plurality of machine learning models, wherein the providing comprises filtering information associated with the behavioral event prediction based on a confidence threshold associated with the first one of the plurality of machine learning models.

13. The computing system of claim 11, wherein the second processor is further configured to execute the instructions to train the first one of the plurality of machine learning models, and wherein the second processor is configured to train the first one of the plurality of machine learning models by:

receive data describing user behavior for users of a user population; and generate instances of training data, wherein the second processor being configured to generate the instances of training data comprises the second processor being configured to:

select behavior data exhibiting a common pattern useable to describe a response to an event for at least one user of the user population;

define an event profile for the event, the event profile specifying a type of the event and the response to the event; and train the first one of the plurality of machine learning models to predict occurrence of the event using the instances of training data, wherein the second processor being configured to train the first one of the plurality of machine learning models to predict the occurrence of the event using the instances of training data comprises the second processor being configured to:

provide the instances of training data to the first one of the plurality of machine learning models;

receive, for each instance of training data, an event prediction from the first one of the plurality of machine learning models indicating whether the event will occur over time encompassed by the instance of training data;

compare, for each instance of training data, the event prediction to the event profile; and adjust at least one weight of the first one of the plurality of machine learning models based on the comparing.

14. The computing system of claim 11, wherein the second processor is further configured to execute the instructions to:

generate at least the second one of the plurality of machine learning models based on glucose measurements of a user population; and generate at least the first one of the plurality of machine learning models based on additional data of the user population.

15. The computing system of claim 11, wherein:

the second processor is further configured to execute the instructions to:

generate a third one of the plurality of machine learning models based on glucose measurements of a user population; and generate a fourth one of the plurality of machine learning models based on additional data of the user population; and the first processor is further configured to execute the instructions to:

cause the third one of the plurality of machine learning models generated based on the glucose measurements of the user population to output a first initial glucose measurement prediction;

provide the first initial glucose measurement prediction as input to the fourth one of the plurality of machine learning models generated based on the additional data of the user population;

cause the fourth one of the plurality of machine learning models generated based on the additional data of the user population to output a second initial glucose measurement prediction; and provide the second initial glucose measurement prediction as input to the first one of the plurality of machine learning models or the second one of the plurality of machine learning models.

16. The computing system of claim 11, wherein:

the second processor is further configured to execute the instructions to:

generate a third one of the plurality of machine learning models based on glucose measurements of a user population; and generate a fourth one of the plurality of machine learning models based on additional data of the user population; and the first processor is further configured to execute the instructions to:

cause the fourth one of the plurality of machine learning models generated based on the additional data of the user population to generate an instance of training data;

provide the instance of training data as input to the third one of the plurality of machine learning models generated based on the glucose measurements of the user population;

cause the third one of the plurality of machine learning models generated based on the glucose measurements of the user population to output an event profile for the instance of training data; and provide the event profile and the instance of training data as input to the first one of the plurality of machine learning models or the second one of the plurality of machine learning models.

17. The computing system of claim 11, wherein the second processor is further configured to execute the instructions to generate the first one of the plurality of machine learning models, and wherein the second processor is configured to generate the first one of the plurality of machine learning models by:

receive historical glucose measurements of a user population, the historical glucose measurements provided by continuous glucose monitoring systems worn by users of the user population;

generate instances of training data by selecting, for each instance of training data, glucose measurements from the historical glucose measurements and generate an event profile defining the instance of training data as including an event and glucose level changes relative to the activity; and train the first one of the plurality of machine learning models to predict occurrence of the activity using the instances of training data and the corresponding event profiles.

18. The computing system of claim 11, wherein the second one of the plurality of machine learning models is a recurrent neural network configured to iteratively generate the glucose measurement prediction, each iteration generating measurements for a portion of the glucose measurement prediction.

19. The computing system of claim 18, wherein the first one of the plurality of machine learning models is a reinforcement learning model updated on feedback regarding the behavioral event prediction.

20. The computing system of claim 11, wherein the glucose measurements include at least one current glucose measurement.

* * * * *